United States Patent
Wada et al.

(10) Patent No.: US 6,310,049 B1
(45) Date of Patent: Oct. 30, 2001

(54) NEMATICIDAL PYRAZOLES

(75) Inventors: Katsuaki Wada, Tochigi; Takuya Gomibuchi, Ibaraki; Yuichi Otsu; Katsuhiko Shibuya, both of Tochigi; Takahisa Abe, Hokkaido, all of (JP); Wolfram Andersch, Bergisch Gladbach (DE); Achim Harder, Köln (DE); Peter Lösel, Monheim (DE)

(73) Assignee: Nihon Bayer Agrochem K.K., Tokyo (JP)

(*) Notice: Subject to any disclaimer, the term of this patent is extended or adjusted under 35 U.S.C. 154(b) by 0 days.

(21) Appl. No.: 09/762,365

(22) PCT Filed: Aug. 3, 1999

(86) PCT No.: PCT/EP99/05684

§ 371 Date: Apr. 5, 2001

§ 102(e) Date: Apr. 5, 2001

(87) PCT Pub. No.: WO00/09500

PCT Pub. Date: Feb. 24, 2000

(30) Foreign Application Priority Data

Aug. 11, 1998 (JP) .................................................. 10/237958
Feb. 17, 1999 (JP) .................................................. 11/038596
Jun. 15, 1999 (JP) .................................................. 11/168117

(51) Int. Cl.[7] ..................... A61K 31/4155; C07D 409/04

(52) U.S. Cl. ........................... 514/63; 514/406; 548/110; 548/365.7

(58) Field of Search ................................ 548/365.7, 110; 514/63, 406

(56) References Cited

U.S. PATENT DOCUMENTS

| | | | |
|---|---|---|---|
| 3,991,073 | 11/1976 | Mulder et al. | 260/310 D |
| 4,122,200 | 10/1978 | Briet et al. | 424/275 |
| 4,645,796 | 2/1987 | Beyer et al. | 525/84 |

FOREIGN PATENT DOCUMENTS

| | | |
|---|---|---|
| 56-123904 | 9/1981 | (JP) . |
| 87/06429 | 11/1987 | (WO) . |

OTHER PUBLICATIONS

Zh. Org. Khim., vol. 15, No. 1, pp. 57–63, Jan. 1979, V.N. Elokhina, R.V. Karnaukhova, A.S. Nakhmanovich, I.D. Kalikhman, and M.G. Voronkov, Reaction of 1,2-Ethanedithiol with a-Acetylenic Ketones.
J. of Electron Spectroscopy and Related Phenomena, 31 (4), (month unavailable) 1983, pp. 317–321, A. Katrib, N.R. El-Rayyes and F.M. Al-Kharafi, N 1s Orbital Binding Energies of some Pyrazole and Pyrazoline Compounds by XPS.

J. Org. Chem. 63(4), (month unavailable) 1998, pp. 1109–1118, Leo S. Bleicher, Nicholas D.P. Cosford, Audrey Herbaut, J. Stuart McCallum and Ian A. McDonald, A Practical and Efficient Synthesis of the Selective Neuronal Acetylcholine–Gated Ion Channel Agonist (S)–(—)–5–Ethynyl–3–(1–methyl–2–pyrrolidinyl)pyridine Maleate (SIB–1508Y).
J. Chem. Res. Synop (1) pp. 4 and 5, (month unavailable) 1995, Nitya G. Kundu, Manojit Pal And Chinmay Chowdhury, A High Simplidied approach for Synthesis of β–Arylsubstituted Conjugaed Acetylenic Ketonne Mediated through Palladium–Copper Catalysis.
J. Am. Chem. Soc., 69, Aug. 1947, pp. 2017–2018, Phyllis Rutan and Clarence E. May, Concerning Aromatic Acetylenic Carbinols.
J. Amer. Chem. Soc., vol. 72, pp. 5219–5220, Nov. 1950, James K. Sneed and Robert Levine, Condensations Effected by The Alkali Amides, VI. Studies in the Acylation of Methyl 2–Thienyl Ketone.
Indian Journal of Chem., vol. 32B, Nov. 1993, pp. 1125–1129, Ali A. Khalaf, Reda A. Kabli, M.T. Zimaity, A.M. Khalil, A.M. Kaddah & H.A. Al–Rifaie, N–Derivatisation of some 3–2(2–furyl)–and 3–(2–thienyl)–5–aryl–2–pyrazolines.

(List continued on next page.)

Primary Examiner—Laura L. Stockton
(74) Attorney, Agent, or Firm—Joseph C. Gil; Jackie Ann Zurcher

(57) ABSTRACT

(I)

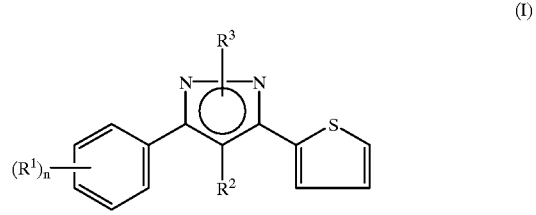

Novel pyrazoles of formula (1) wherein $R^1$ represents halogen, $C_{1-6}$ alkyl, $C_{1-5}$ haloalkyl, $C_{2-6}$ alkoxy, $C_{1-4}$ alkylthio, $C_{2-5}$ alkenyloxy, $C_{3-5}$ alkynyloxy, $C_{2-6}$ (total carbon number) alkoxyalkyl, $C_{2-6}$ (total carbon number) alkylthioalkyl, $C_{1-5}$ haloalkoxy, $C_{2-6}$ (total carbon number) alkoxyalkoxy, hydroxy or optionally substituted phenyl, $R^2$ represents hydrogen, halogen, $C_{1-5}$ alkyl, $C_{2-6}$ (total carbon number) alkoxyalkyl, $C_{2-6}$ (total carbon number) alkylthioalkyl, $C_{2-6}$ (total carbon number) alkylsulfinylalkyl, $C_{2-6}$ (total carbon number alkylsulfonylalkyl or $C_{1-5}$ haloalkyl, $R^3$ represents hydrogen, $C_{1-5}$ alkyl, —$COR^4$, $COOR^5$, $CH(OR^6)_2$ or $CH_2Si(R^7)_3$, $R^4$ represents $C_{1-10}$ alkyl, $C_{1-6}$ haloalkyl, $C_{2-6}$ alkenyl, optionally substituted $C_{3-6}$ cycloalkyl, $C_{2-6}$ (total carbon number) alkoxyalkyl, $C_{2-6}$ (total carbon number alkylthioalkyl, optionally substituted phenyl, $C_{1-6}$ haloalkyl, alkylamino, di-($C_{1-6}$ alkyl)amino or optionally substituted phenylamino, $R^5$ represents $C_{1-7}$ alkyl, $R^6$ and $R^7$ represent $C_{1-6}$ alkyl, and n is 1, 2 or 3, and when n is 2 or 3, the corresponding number (n) of $R^1$ radicals may be the same or different, processes for preparing these compounds and their use as nematicides and anthelmintics.

14 Claims, No Drawings

OTHER PUBLICATIONS

J. Indian Chem. Soc., vol. 68, Jan. 1991, pp. 47–51, Reda A Kabli, Ali A. Khalaf, M.T. Zimaity, A.M. Khalil, A.M. Kaddah and H. A. Al–Rifaie, Synthesis of a New Series of Furyl and Thienyl subtstituted Pyrazolines Starting with Furyl and Thienyl Chalcones.

Arch. Pharm. 329(12), (month unavailable) 1996, pp. 529–534, Flavia Varano, Daniela Catarzi, Vittoria Colotta, Lucia Cecchi, Guido Filacchioni, Alessandro Galli and Chiara Costagli, Structure,–Activity Relationship Studies of Novel Pyrazolo[1,5–c]1,3]benzoxazines: Synthesis and Benzodiazepine Receptor Affinity.

J. Indian Chem. Soc., 64, Jul. 1987, pp. 408–410, Kumkum Agrawal, Oxidation of Pyrazolines with Manganes Dioxide.

**Database Chemabs, Chemical Abstracts, Varano, Flavia et al: Structure–activity relationship Studies of novel pyrazolo(1,5,–c!1,3!benzoxazine. Synthesis and benzodiazepine receptor affinity: retrieved from STN Database accesion No. 126:171535, XP002134797, 2–'5–(2–thienyl)–1H–pyrazol–3–yl ! phenol (RN=187173–74–6) & Arch. Pharm. (Weinheim Ger.) (1996), 329(12), 529–534.

**Chemical Abstracts, vol. 110, No. 17, Apr. 24, 1989, Abstract No. 154064, Gupta, D.P. et al.

"Synthesis anthelmintic and antiacetylcholinesterase activity of newer furan derivatives" XP992134796 abstract & Indian J. Pharm Sci. (1988), 50(2) 98–100, 112.

**Database Chemabs, Chemical Abstracts, Sarbaggya, D.P. et al, "Synthesis of some 2–furyl Land 2–furyl and 2–thienyl chromones" retrieved from STN Database accession No. 95:24725 XP002134866 compounds with RN=77708–31–7; 77708–32–8; 78095–59–7 & J. Indian Chem. Soc. (1981), 58(2), 196–7.

** Database Chemabs, Chemical Abstracts, Rangachari, K. et al: "synthesis of some 2–(2'–Thienoyl)coumaran–3–ones" retrieved from STN Database accession No. 94:208628 XP002134867 compound with RN=6297–64–9; 7209–69–0; 60072–53–9; 60072–55–1; 77708–31–7; 77708–32–8 & J. Indian Chem. Soc. (1980), 57(10), 1014–16.

**Database Chemabs, Chemical Abstracts, Thakar, K.A. et al; "synthesis of 3–(2'–furyl or 2'Thienyl)–5–(substituted 2"–hydroxyphenyl)isoxazoles" retrieved from STN Database accession No. 85:123800 XP002134868 compouns with RN=57051–63–5; 57051–64–6; 57051–65–7; 57051–66–8; 57051–71–5; 57051–72–6; 60478–00–4; 60478–01–5 & Indian J. Chem., Sect. B (1976), 14B(3) 224–6.

**Database Chemabs, Chemical Abstract, Kulkarni, S.U. et al: "Synthesis of some 1,5–Benzodiazepines, PartII" retrieved from STN Database accession No. 85:63039 XP002134869 Compounds with RN=60072–53–9; 60072–54–0; 60072–55–1; 60072–56–2; 60072–57–3 & J. Indian Chem. Soc. (1976), 53(3), 279–82.

**Database Chemabs, Chemical Abstracts, Thakar, K.A. et al: "Synthesis of thienyl analogs of Substituted flavonoids" retrived from STN Database accession No. 83:178714 XP002134870 compounds ith RN=57051–63–5; 57051–64–6; 57051–65–7; 57051–6608; 57051–7105; 57051–72–6 & J. Indian Chem. Soc. (1975), 52(3), 243–7.

**Database Chemabs, Chemical Abstracts, Thakar, K.A. et al: "Synthesis of 6– and 7–halo–2–(2–thienyl)chromones and related compounds" retrived from STN Database accession No. 78:71841 XP002134871 compounds with RN=39730–38–6; 39730–39–7; 39730–40–0; 39730–41–1; 39730–42–2 & J. Indian Chem. Soc. (1972), 49(10), 1029–33.

** Database Crossfire Online! Beilstein XP002134872 BRN=2518330 & Journal of the Chemical Society., 1947, pp. 1626–1630, Chemical Society, Letchworth., GB.

**Database Crossfire Online! Beilstein XP002134873 BRN=2518328 & Collect. Czech. Chem. Commun., 1960, pp. 1199–1209.

**Database Crossfire Online!Beilstein XP002134874 BRN=2258605 & Eur. J. Med. Chem. Chim. Ther., 1993, pp. 473–480.

**Database Crossfire Online! Beilstein XP002134875 BRN=2519023 & Collect. Czech. Chem. Commun., 1960, pp. 1199–1209.

**Database Crossfire Online! Beilstein XP002134876 BRN=2083714 & Journal of the Chemical Society, Perkin Transactions 1., 1993, pp. 2657–2664, Chemical Society, Letchworth., GB ISSN: 0300–922X.

NEMATICIDAL PYRAZOLES

This application is a 371 of PCT/EP99/05684 filed Aug. 3, 1999.

FIELD OF THE INVENTION

The present invention relates to novel pyrazoles, to processes for their preparation and to their use as nematicides and anthelmintics as well as to the intermediates for the preparation of pyrazoles.

BACKGROUND OF THE INVENTION

Specifically, 3-(2-Thienyl)-5-phenyl-1H-pyrazole has already been disclosed in Zh. Org. Khim., 15(1), 57–63, 1979, and 3-(2-thienyl)-5-(4-methoxyphenyl)-1H-pyrazole has been described in J. Electron Spectrosc. Relat. Phenom., 31(4), 317–21, 1983.

However, it is neither described nor suggested in these publications that the aforesaid compounds have a nematicidal action.

Moreover, a certain kind of insecticidal oxazole or thiazole derivatives have already been disclosed in WO 87/06429, and insecticidal bithienyl derivatives have been described in WO 86/05949.

SUMMARY OF THE INVENTION

Pyrazoles of the formula (I)

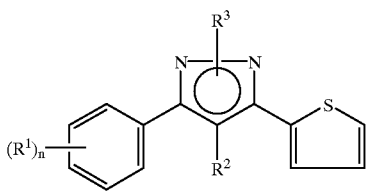

(I)

wherein
- $R^1$ represents halogen, $C_{1-6}$ alkyl, $C_{1-5}$ haloalkyl, $C_{2-6}$ alkoxy, $C_{1-4}$ alkylthio, $C_{2-5}$ alkenyloxy, $C_{3-5}$ alkynyloxy, $C_{2-6}$ (total carbon number) alkoxyalkyl, $C_{2-6}$ (total carbon number) alkylthioalkyl, $C_{1-5}$ haloalkoxy, $C_{2-6}$ (total carbon number) alkoxyalkoxy, hydroxy or optionally substituted phenyl,
- $R^2$ represents hydrogen, halogen, $C_{1-5}$ alkyl, $C_{2-6}$ (total carbon number) alkoxyalkyl, $C_{2-6}$ (total carbon number) alkylthioalkyl, $C_{2-6}$ (total carbon number) alkylsulfinylalkyl, $C_{2-6}$ (total carbon number) alkylsulfonylalkyl or $C_{1-5}$ haloalkyl,
- $R^3$ represents hydrogen, $C_{1-5}$ alkyl, —$COR^4$, —$COOR^5$, $CH(OR^6)_2$, or $CH_2Si(R^7)_3$,
- $R^4$ represents $C_{1-10}$ alkyl, $C_{1-6}$ haloalkyl, $C_{2-6}$ alkenyl, optionally substituted $C_{3-6}$ cycloalkyl, $C_{2-6}$ (total carbon number) alkoxyalkyl, $C_{2-6}$ (total carbon number) alkylthioalkyl, optionally substituted phenyl, $C_{1-5}$ alkylamino, di-($C_{1-6}$ alkyl) amino or optionally substituted phenylamino,
- $R^5$ represents $C_{1-7}$ alkyl,
- $R^6$ and $R^7$ represent $C_{1-6}$ alkyl, and
- n is 1, 2 or 3, and when n is 2 or 3, the $R^1$ radicals may be the same or different.

DETAILED DESCRIPTION

There have now been found novel pyrazoles of the formula (I)

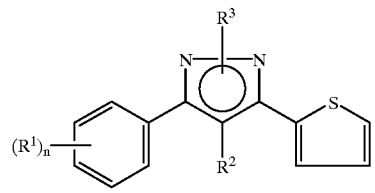

(I)

wherein
- $R^1$ represents halogen, $C_{1-6}$ alkyl, $C_{1-5}$ haloalkyl, $C_{2-6}$ alkoxy, $C_{1-4}$ alkylthio, $C_{2-5}$ alkenyloxy, $C_{3-5}$ alkynyloxy, $C_{2-6}$ (total carbon number) alkoxyalkyl, $C_{2-6}$ (total carbon number) alkylthioalkyl, $C_{1-5}$ haloalkoxy, $C_{2-6}$ (total carbon number) alkoxyalkoxy, hydroxy or optionally substituted phenyl,
- $R^2$ represents hydrogen, halogen, $C_{1-5}$ alkyl, $C_{2-6}$ (total carbon number) alkoxyalkyl, $C_{2-6}$ (total carbon number) alkylthioalkyl, $C_{2-6}$ (total carbon number) alkylsulfinylalkyl, $C_{2-6}$ (total carbon number) alkylsulfonylalkyl or $C_{1-5}$ haloalkyl,
- $R^3$ represents hydrogen, $C_{1-5}$ alkyl, —$COR^4$, —$COOR^5$, $CH(OR^6)_2$, or $CH_2Si(R^7)_3$,
- $R^4$ represents $C_{1-10}$ alkyl, $C_{1-6}$ haloalkyl, $C_{2-6}$ alkenyl, optionally substituted $C_{3-6}$ cycloalkyl, $C_{2-6}$ (total carbon number) alkoxyalkyl, $C_{2-6}$ (total carbon number) alkylthioalkyl, optionally substituted phenyl, $C_{1-5}$ alkylamino, di-($C_{1-6}$ alkyl)amino or optionally substituted phenylamino,
- $R^5$ represents $C_{1-7}$ alkyl,
- $R^6$ and $R^7$ represent $C_{1-6}$ alkyl, and
- n is 1, 2 or 3, and when n is 2 or 3,
- the corresponding number (n) of $R^1$ radicals may be the same or different.
  (i) When $R^3$ is not H, the compound of the above formula (I) can exist as a mixture of the following positional isomers

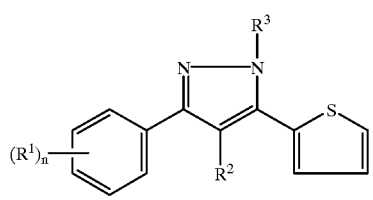

(Ia)

wherein $R^1$, $R^2$, $R^3$ and n are as defined above, and

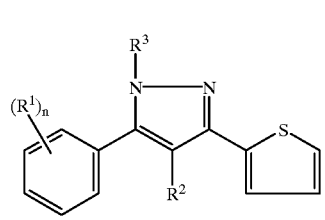

(Ib)

wherein $R^1$, $R^2$, $R^3$ and n are as defined above.

(ii) When $R^3$ is H, the compound of the above formula (I) can exist as a mixture of the following tautomers:

(Ic)

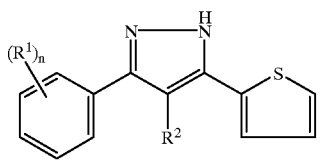

wherein $R^1$, $R^2$ and n are as defined above, and (Id)

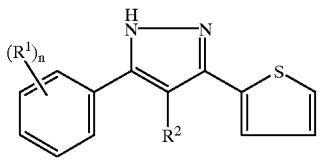

wherein $R^1$, $R^2$ and n are as defined above.

The compounds of formula (I) can be obtained by a process in which a) when $R^3$ is hydrogen:
compounds of the formula (II)

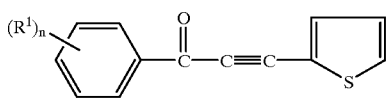

wherein $R^1$ and n are as defined above, are reacted with a compound of the formula

 (III)

in the presence of suitable diluent, and if appropriate in the presence of an acid catalyst, or b) when $R^3$ is hydrogen:
compounds of the formula (IV)

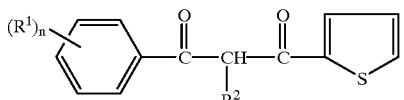

wherein $R^1$, $R^2$ and n are as defined above, are reacted with the aforementioned compound of the formula (III) in the presence of suitable diluent, and if appropriate, in the presence of an acid catalyst, or c) when $R^3$ is a radical as defined above but other than hydrogen:
compounds of formula (V)

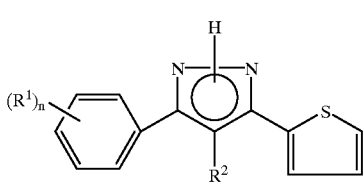

wherein $R^1$, $R^2$ and n are as defined above, are reacted with compounds of the formula

 (VI)

wherein $R^3$ is a radical as defined above but other than hydrogen, and X is halogen, in the presence of suitable diluent, and if appropriate, in the presence of an acid binding agent, or d) compounds of the formulae (VIIa)

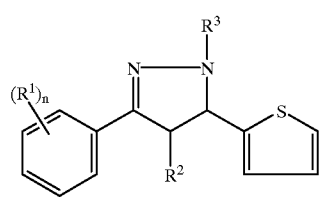

or (VIIb)

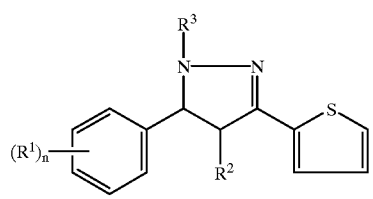

wherein $R^1$, $R^2$, $R^3$ and n are as defined above. are oxidized, or e) when $R^2$ is alkylsulfinylalkyl or alkylsulfonylalkyl compounds of the formula (VIII)

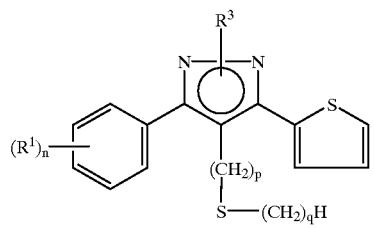

wherein $R^1$, $R^3$ and n are as defined above, p is 1, 2 or 3, q is 1, 2, 3, 4 or 5, and $2 \leq p+q \leq 6$, are oxidized.

The compounds of formula (I) according to the present invention have strong nematicidal activities and anthelmintic activities. In particular, they exhibit a very excellent nematicidal and anthelmintic effects as compared with the aforesaid well-known 3-(2-thienyl)-5-phenyl-1H-pyrazole and 3-(2-thienyl)-5-(4- methoxyphenyl)-1H-pyrazole, and also have a good affinity for crops and mammals. Accordingly, the compounds of the present invention are very useful as nematicides and anthelmintics.

In this specification, the "halogen" and the halogen in the "haloalkyl" and the "haloalkoxy" means fluoro, chloro, bromo or iodo.

The "alkyl" may be straight-chain or branched, and includes, for example, methyl, ethyl, propyl, isopropyl, n-, iso-, sec- or tert-butyl, n-, iso-, neo- or tert-pentyl, n- or isohexyl, heptyl, octyl, nonyl and decyl.

The "haloalkyl" may be straight-chain or branched, and includes, for example, chloromethyl, 2-chloroethyl, trifluoromethyl, 2,2,2-trifluoroethyl and 2,2,3,3-tetrafluoropropyl.

The "alkoxy" may be straight-chain or branched, and includes, for example, ethoxy, propoxy, isopropoxy, n-, iso-, sec- or tert-butoxy, pentyloxy and hexyloxy.

The "alkylthio" may be straight-chain or branched, and includes, for example, methylthio, ethylthio, propylthio, isopropylthio, and n-, iso-, sec- or tert-butylthio.

The "alkenyloxy" includes, for example, vinyloxy, allyloxy, 1-propenyloxy, isopropenyloxy and 1-, 2- or 3-butenyloxy.

The "alkynyloxy" includes, for example, propargyloxy.
The "alkoxyalkyl" includes, for example, methoxymethyl, ethoxymethyl, propoxymethyl, isopropoxymethyl, n-, iso-, sec- or tert-butoxymethyl, and n-, iso-, sec-, tert- or neo-pentoxymethyl.

The "alkylthioalkyl" includes, for example, methylthiomethyl, ethylthiomethyl, propylthiomethyl, isopropylthiomethyl, n-, iso-, sec- or tert-butylthiomethyl, n-, iso-, sec-, tert- or neo-pentylthiomethyl, and methylthioethyl.

The "haloalkoxy" includes, for example, difluoromethoxy, trifluoromethoxy, chlorodifluoromethoxy, 2,2,2-trifluoroethoxy and 2,2,3,3-tetrafluoropropyloxy.

The "alkoxyalkoxy" includes, for example, methoxymethoxy and ethoxymethoxy.

The "alkylsulfinylalkyl" includes, for example, methylsulfinylmethyl, ethylsulfinylmethyl, propylsulfinylmethyl, isopropylsulfinylmethyl and methylsulfinylethyl.

The "alkylsulfonylalkyl" includes, for example, methylsulfonylmethyl, ethylsulfonylmethyl, propylsulfonylmethyl, isopropylsulfonylmethyl and methylsulfonylethyl.

The "cycloalkyl" includes, for example, cyclopropyl, cyclobutyl, cyclopentyl and cyclohexyl.

The "fluoro-substituted cyclopropyl" includes, for example,2,2-difluorocyclopropyl.

The "optionally substituted phenyl" includes, for example, phenyl, 4-fluorophenyl, 4-trifluoromethylphenyl, 4-chlorophenyl, 4-trifluoromethoxyphenyl, (4-fluorophenyl)-phenyl and (4-trifluoromethylphenyl) phenyl.

The "alkylamino" includes, for example, methylamino, ethylamino, propylamino, isopropylamino, n-, iso-, sec- or tert-butylamino, and n-, iso-, sec-, tert- or neo-pentylamino.

The "dialkylamino" includes, for example, dimethylamino, diethylamino and di(n- or iso-)propylamino.

The "optionally substituted phenylamino" includes, for example, phenylamino, 4-fluorophenylamino, 4-chlorophenylamino and 4-trifluoromethylphenylamino.

Among the compounds of the formula (I), according to the invention, preferred compounds are those in which:

$R^1$ represents fluoro, chloro, bromo, iodo, $C_{1-4}$ alkyl, $C_{1-3}$ haloalkyl, $C_{2-4}$ alkoxy, $C_{1-3}$ alkylthio, $C_{2-3}$ alkenyloxy, $C_{3-4}$ alkynyloxy, $C_{2-4}$ (total carbon number) alkoxyalkyl, $C_{2-4}$ (total carbon number) alkylthioalkyl, $C_{1-3}$ haloalkoxy, $C_{2-4}$ (total carbon number) alkoxyalkoxy, hydroxy, optionally halogen-substituted phenyl or optionally $C_{1-3}$ alkyl-substituted phenyl, $R^2$ represents hydrogen, fluoro, chloro, bromo, $C_{1-4}$ alkyl, $C_{2-4}$ (total carbon number) alkoxyalkyl, $C_{2-4}$ (total carbon number) alkylthioalkyl, $C_{2-4}$ (total carbon number) alkylsulfinylalkyl, $C_{2-4}$ (total carbon number) alkylsulfonylalkyl or $C_{1-3}$ haloalkyl, $R^3$ represents hydrogen, $C_{1-5}$ alkyl, —$COR^4$, —$COOR^5$, $CH(OR^6)_2$ or $CH_2Si(R^7)_3$, $R^4$ represents $C_{1-5}$ alkyl, $C_{1-4}$ haloalkyl, $C_{2-3}$ alkenyl, cyclopropyl, fluoro-substituted cyclopropyl, $C_{2-4}$ (total carbon number) alkoxyalkyl, $C_{2-4}$ (total carbon number) alkylthioalkyl, optionally halogen-substituted phenyl, optionally $C_{1-3}$ fluoroalkyl-substituted phenyl, $C_{1-3}$ alkylamino, di-($C_{1-4}$ alkyl)amino or optionally chloro-substituted phenylamino, $R^5$ represents $C_{1-5}$ alkyl, $R^6$ and $R^7$ represent $C_{1-4}$ alkyl, and n is 1, 2 or 3, and when n is 2 or 3, $R^1$ radicals may be the same or different.

Particularly preferred compounds of the formula (I) are those in which:

$R^1$ represents fluoro, chloro, bromo, iodo, $C_{1-4}$ alkyl, fluoro-substituted $C_{1-3}$ alkyl, $C_{2-3}$ alkoxy, $C_{1-2}$ alkylthio, allyloxy, propargyloxy, $C_{2-3}$ (total carbon number) alkoxyalkyl, $C_{2-3}$ (total carbon number) alkylthioalkyl, fluoro-substituted $C_{1-3}$ alkoxy, $C_{2-3}$ (total carbon number) alkoxyalkoxy, hydroxy or optionally fluoro- or methyl-substituted phenyl.

$R^2$ represents hydrogen, fluoro, chloro, bromo, $C_{1-4}$ alkyl, $C_{2-3}$ (total carbon number) alkoxyalkyl, $C_{2-3}$ (total carbon number) alkylthioalkyl, $C_{2-3}$ (total carbon number) alkylsulfinylalkyl, $C_{2-3}$ (total carbon number) alkylsulfonylalkyl or fluoro-substituted $C_{1-3}$ alkyl, $R^3$ represents hydrogen, $C_{1-4}$ alkyl, —$COR^4$, —$COOR^5$, $CH(OR^6)_2$ or $CH_2Si(R^7)_3$, $R^4$ represents $C_{1-5}$ alkyl, $C_{1-4}$ haloalkyl, $C_{2-3}$ alkenyl, cyclopropyl, fluoro-substituted cyclopropyl, $C_{2-3}$ (total carbon number) alkoxyalkyl, $C_{2-3}$ (total carbon number) alkylthioalkyl, optionally fluoro-substituted phenyl, optionally trifluoromethyl-substituted phenyl, $C_{1-2}$ alkylamino, di-($C_{1-2}$ alkyl)amino or optionally para-chloro-substituted phenylamino, $R^5$ represents $C_{1-4}$ alkyl, $R^6$ represents $C_{1-2}$ alkyl, $R^7$ represents methyl and n is 1, 2 or 3, and when n is 2 or 3, $R^1$ radicals may be the same or different.

For example, when 1-(4-chlorophenyl)-3-(2-thienyl)-2-propyn-1-one and hydrazine are used as the starting materials in the above-described method (a) for preparing a compound of formula (I), the preparation method (a) is represented by the following reaction formula:

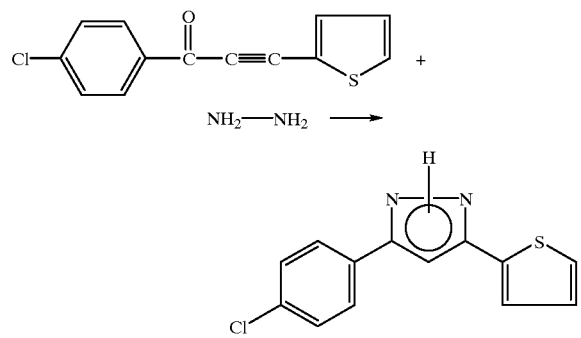

For example, when 1-(4-chlorophenyl)-3-(2-thienyl)-1,3-propanedione and hydrazine are used as the starting materials in the above-described method (b) for preparing a compound of formula (I), the preparation method (b) is represented by the following reaction formula:

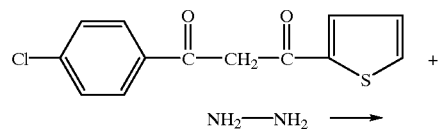

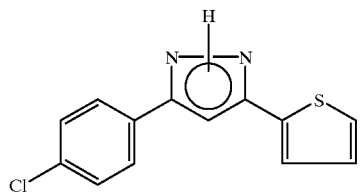

For example, when 3-(2-thienyl)-5-(4-chlorophenyl)-1H-pyrazole and acetyl chloride are used as the starting materials in the above-described method (c) for preparing a compound of formula (I), the preparation method (c) is represented by the following reaction formula:

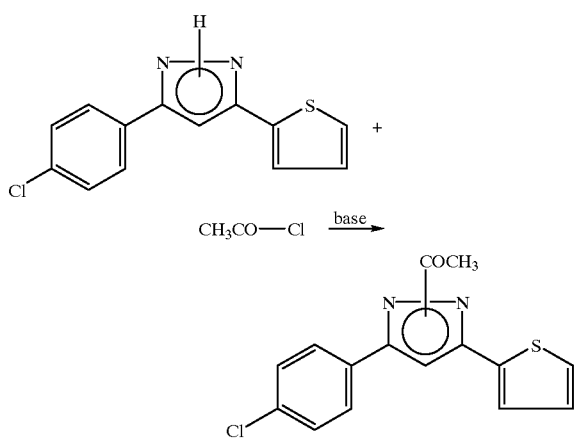

For example, when 3-(4-chlorophenyl)-5-(2-thienyl)-pyrazoline is used as the starting material and oxidized with the aid of active manganese dioxide in the above-described method (d) for preparing a compound of formula (I), the preparation method (d) is represented by the following reaction formula:

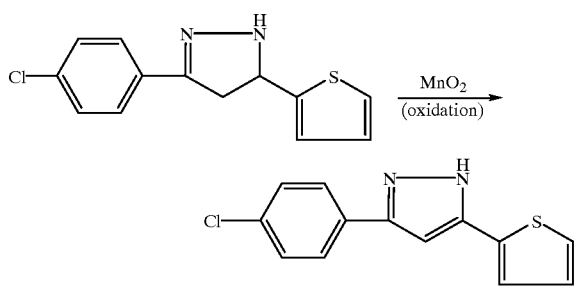

For example, when 3-(4-chlorophenyl)-4-methylmercapto-methyl-5-(2-thienyl)-1H-pyrazole is used as the starting material and oxidized with the aid of hydrogen peroxide in the above-described method (e) for preparing a compound of formula (I) in which $R^2$ is alkylsulfinyl or alkylsulfonyl, the preparation method (e) is represented by the following reaction formula:

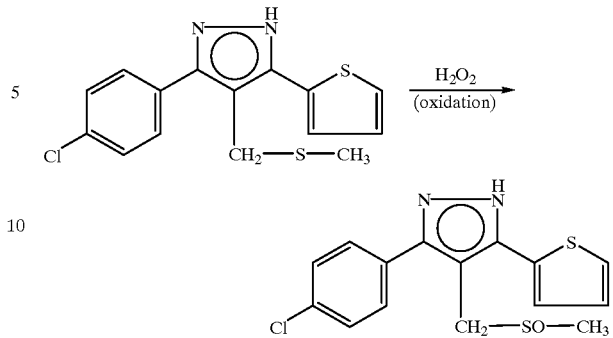

The compound of formula (II) used as a starting material in the above-described preparation method (a) is a novel compound which has not been described in the literature of the prior art. Generally, the compounds of formula (II) may be prepared, for example, by the preparation method (f) described below.

Preparation Method (f)

A method which comprises oxidizing a compound of the formula

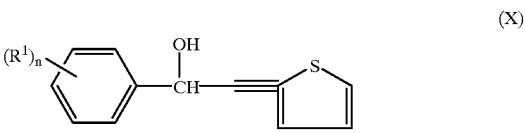

(X)

wherein $R^1$ and n are as defined above.

The compounds of the above formula (X) are novel compounds which have not been described in the literature of the prior art, and may be prepared, for example, by the preparation method (g) described below. As compounds of formula (X) in which $R^1$ is hydrogen, 1-(phenyl)-3-(2-thienyl)-2-propyn-1-ol is described in J. Org. Chem., 63(4), 1109–1118 (1998), and 1-(4-methoxyphenyl)-3-(2-thienyl)-2-propyn-1-ol is described in J. Chem. Res., Synop. (1), 4–5 (1995).

Preparation Method (g)

A method which comprises reacting a compound of the formula

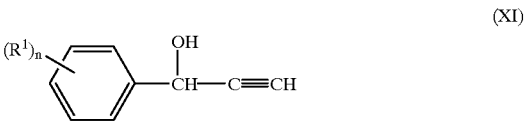

(XI)

wherein $R^1$ and n are as defined above, with a compound of the formula (XII)

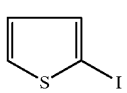

Typical examples of the compounds of the above formula (X) are as follows:

1-(2-Fluorophenyl)-3-(2-thienyl)-2-propyn-1-ol,
1-(2-chlorophenyl)-3-(2-thienyl)-2-propyn-1-ol,
1-(2-trifluoromethylphenyl)-3(2-thienyl)-2-propyn-1-ol,
1-(3-chlorophenyl)-3-(2-thienyl)-2-propyn-1-ol,
1-(3-methylphenyl)-3-(2-thienyl)-2-propyn-1-ol,
1-(4-fluorophenyl)-3-(2-thienyl)-2-propyn-1-ol,
1-(4-chlorophenyl)-3-(2-thienyl)-2-propyn-1-ol,
1-(4-bromophenyl)-3-(2-thienyl)-2-propyn-1-ol,
1-(4-iodophenyl)-3-(2-thienyl)-2-propyn-1-ol,
1-(4-methylphenyl)-3-(2-thienyl)-2-propyn-1-ol,
1-(4-ethylphenyl)-3-(2-thienyl)-2-propyn-1-ol,
1-(4-propylphenyl)-3-(2-thienyl)-2-propyn-1-ol,
1-(4-isopropylphenyl)-3-(2-thienyl)-2-propyn-1-ol,
1-(4-butylphenyl)-3-(2-thienyl)-2-propyn-1-ol,
1-(4-tert-butylphenyl)-3-(2-thienyl)-2-propyn-1-ol,
1-(4-trifluoromethylphenyl)-3-(2-thienyl)-2-propyn-1-ol,
1-(4-ethoxyphenyl)-3-(2-thienyl)-2-propyn-1-ol,
1-(4-propoxyphenyl)-3-(2-thienyl)-2-propyn-1-ol,
1-(4-methylmercaptophenyl)-3-(2-thienyl)-2-propyn-1-ol,
1-(4-allyloxyphenyl)-3-(2-thienyl)-2-propyn-1-ol,
1-(4-propargyloxyphenyl)-3-(2-thienyl)-2-propyn-1-ol,
1-(4-methoxymethylphenyl)-3-(2-thienyl)-2-propyn-1-ol,
1-(4-ethoxymethylphenyl)-3-(2-thienyl)-2-propyn-1-ol,
1-(4-methylmercaptomethylphenyl)-3-(2-thienyl)-2-propyn-1-ol,
1-(4-difluoromethoxyphenyl)-3-(2-thienyl)-2-propyn-1-ol,
1-(4-trifluoromethoxyphenyl)-3-(2-thienyl)-2-propyn-1-ol,
1-[4-(2,2,2-trifluoroethoxy)phenyl]-3-(2-thienyl)-2-propyn-1-ol,
1-[4-(2,2,3,3-tetrafluoropropyloxy)phenyl]-3-(2-thienyl)-2-propyn-1-ol,
1-(4-methoxymethoxyphenyl)-3-(2-thienyl)-2-propyn-1-ol,
1-(4-hydroxyphenyl)-3-(2-thienyl)-2-propyn-1-ol,
1-(4-phenylphenyl)-3-(2-thienyl)-2-propyn-1-ol,
1-[4-(4-fluorophenyl)phenyl]-3-(2-thienyl)-2-propyn-1-ol,
1-[4-(4-methylphenyl)phenyl]-3-(2-thienyl)-2-propyn-1-ol,
1-(2,4-dichlorophenyl)-3-(2-thienyl)-2-propyn-1-ol,
1-(3,4-dichlorophenyl)-3-(2-thienyl)-2-propyn-1-ol,
1-(3,5-dichlorophenyl)-3-(2-thienyl)-2-propyn-1-ol,
1-(2,6-difluorophenyl)-3-(2-thienyl)-2-propyn-1-ol,
1-(2,4-difluorophenyl)-3-(2-thienyl)-2-propyn-1-ol,
1-(3,4-difluorophenyl)-3-(2-thienyl)-2-propyn-1-ol,
1-(2,4,6-trifluorophenyl)-3-(2-thienyl)-2-propyn-1-ol,
1-(2,4,6-trichlorophenyl)-3-(2-thienyl)-2-propyn-1-ol, and
1-(2,6-difluoro-4-trifluoromethylphenyl)-3-(2-thienyl)-2-propyn-1-ol.

The compounds of the above formula (XI) are also novel compounds which have not been described in the literature of the prior art, and may be prepared, for example, by the preparation method (h) described below.

As compounds of formula (XI) in which $R^1$ is hydrogen, 4-chloro or 4-methoxy, 1-(phenyl)-2-propyn-1-ol, 1-(4-chlorophenyl)-2-propyn-1-ol and 1-(4-methoxyphenyl)-2-propyn-1-ol are described in J. Am. Chem. Soc., 69, 2017 (1947).

Preparation Method (h)

A method which comprises reacting a compound of the formula

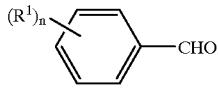

(XIII)

wherein $R^1$ and n are as defined above, with a compound of the formula

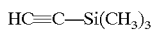

$HC \equiv C—Si(CH_3)_3$ (XIV)

In the above-described preparation method (h), the compounds of formulae (XIII) and (XIV) are compounds which are well known in the field of organic chemistry, and may readily be prepared by any well-known method.

Typical examples of the compounds of the above formula (XI) are as follows:

1-(2-Fluorophenyl)-2-propyn-1-ol,
1-(2-chlorophenyl)-2-propyn-1-ol,
1-(2-trifluoromethylphenyl)-2-propyn-1-ol,
1-(3-chlorophenyl)-2-propyn-1-ol,
1-(3-methylphenyl)-2-propyn-1-ol,
1-(4-fluorophenyl)-2-propyn-1-ol,
1-(4-bromophenyl)-2-propyn-1-ol,
1-(4-iodophenyl)-2-propyn-1-ol,
1-(4-methylphenyl)-2-propyn-1-ol,
1-(4-ethylphenyl)-2-propyn-1-ol,
1-(4-propylphenyl)-2-propyn-1-ol,
1-(4-isopropylphenyl)-2-propyn-1-ol,
1-(4-butylphenyl)-2-propyn-1-ol,
1-(4-tert-butylphenyl)-2-propyn-1-ol,
1-(4-trifluoromethylphenyl)-2-propyn-1-ol,
1-(4-ethoxyphenyl)-2-propyn-1-ol,
1-(4-propoxy phenyl)-2-propyn-1-ol,
1-(4-methylmercaptophenyl)-2-propyn-1-ol,
1-(4-allyloxyphenyl)-2-propyn-1-ol,
1-(4-propargyloxyphenyl)-2-propyn-1-ol,
1-(4-methoxymethylphenyl)-2-propyn-1-ol,
1-(4-ethoxymethylphenyl)-2-propyn-1-ol,
1-(4-methylmercaptomethylphenyl)-2-propyn-1-ol,
1-(4-difluoromethoxyphenyl)-2-propyn-1-ol,
1-(4-trifluoromethoxyphenyl)-2-propyn-1-ol,
1-[4-(2,2,2-trifluoroethoxy)phenyl]-2-propyn-1-ol,
1-[4-(2,2,3,3-tetrafluoropropyloxy)phenyl]-2-propyn-1-ol,
1-(4-methoxymethoxyphenyl)-2-propyn-1-ol,
1-(4-hydroxyphenyl)-2-propyn-1-ol,
1-(4-phenylphenyl)-2-propyn-1-ol,
1-[4-(4-fluorophenyl)phenyl]-2-propyn-1-ol,
1-[4-(4-methylphenyl)phenyl]-2-propyn-1-ol,
1-(2,4-dichlorophenyl)-2-propyn-1-ol, 1-(3,4-dichlorophenyl)-2-propyn-1-ol,
1-(3,5-dichlorophenyl)-2-propyn-1-ol,
1-(2,6-difluorophenyl)-2-propyn-1-ol,
1-(2,4-difluorophenyl)-2-propyn-1-ol,
1-(3,4-difluorophenyl)-2-propyn-1-ol,
1-(2,4,6-trifluorophenyl)-2-propyn-1-ol,
1-(2,4,6-trichlorophenyl)-2-propyn-1-ol, and
1-(2,6-difluoro-4-trifluoromethylphenyl)-2-propyn-1-ol.

The compounds of the above formula (II) are novel compounds which have not been described in the literature of the prior art. 1-(Phenyl)-3-(2-thienyl)-2-propyn-1-one and 1-(4-methoxyphenyl)-3-(2-thienyl)-2-propyn-1-one, which correspond to the compounds of formula (II) wherein $R^1$ is hydrogen or methoxy, are described in Japanese Patent Kokai Publication Sho 56-123904, and the compounds of formula (II) may be prepared by the preparation method described in the aforementioned Japanese Patent Kokai Publication Sho 56-123904.

Typical examples of the compounds of the above formula (II) are as follows:

1-(2-Fluorophenyl)-3-(2-thienyl)-2-propyn-1-one,
1-(2-chlorophenyl)-3-(2-thienyl)-2-propyn-1-one,
1-(2-trifluoromethylphenyl)-3-(2-thienyl)-2-propyn-1-one,
1-(3-chlorophenyl)-3-(2-thienyl)-2-propyn-1-one,
1-(3-methylphenyl)-3-(2-thienyl)-2-propyn-1-one,
1-(4-fluorophenyl)-3-(2-thienyl)-2-propyn-1-one,
1-(4-chlorophenyl)-3-(2-thienyl)-2-propyn-1-one,
1-(4-bromophenyl)-3-(2-thienyl)-2-propyn-1-one,
1-(4-iodophenyl)-3-(2-thienyl)-2-propyn-1-one,
1-(4-methylphenyl)-3-(2-thienyl)-2-propyn-1-one,
1-(4-ethylphenyl)-3-(2-thienyl)-2-propyn-1-one,
1-(4-propylphenyl)-3-(2-thienyl)-2-propyn-1-one,
1-(4-isopropylphenyl)-3-(2-thienyl)-2-propyn-1-one,
1-(4-butylphenyl)-3-(2-thienyl)-2-propyn-1-one,
1-(4-tert-butylphenyl)-3-(2-thienyl)-2-propyn-1-one,
1-(4-trifluoromethylphenyl)-3-(2-thienyl)-2-propyn-1-one,
1-(4-ethoxyphenyl)-3-(2-thienyl)-2-propyn-1-one,
1-(4-propylphenyl)-3-(2-thienyl)-2-propyn-1-one,
1-(4-methylmercaptophenyl)-3-(2-thienyl)-2-propyn-1-one,
1-(4-allyloxyphenyl)-3-(2-thienyl)-2-propyn-1-one,
1-(4-propargyloxyphenyl)-3-(2-thienyl)-2-propyn-1-one,
1-(4-methoxymethylphenyl)-3-(2-thienyl)-2-propyn-1-one,
1-(4-ethoxymethylphenyl)-3-(2-thienyl )-2-propyn-1-one,
1-(4-methylmercaptomethylphenyl)-3-(2-thienyl)-2-propyn-1-one,
1-(4-difluoromethoxyphenyl)-3-(2-thienyl)-2-propyn-1-one,
1-(4-trifluoromethoxyphenyl)-3-(2-thienyl)-2-propyn-1-one,
1-[4-(2,2,2-trifluoroethoxy)phenyl]-3-(2-thienyl)-2-propyn-1-one,
1-[4-(2,2,3,3-tetrafluoropropyloxy)phenyl]-3-(2-thienyl)-2-propyn-1-one,
1-(4-methoxymethoxyphenyl)-3-(2-thienyl)-2-propyn-1-one,
1-(4-hydroxyphenyl)-3-(2-thienyl)-2-propyn-1-one,
1-(4-phenylphenyl)-3-(2-thienyl)-2-propyn-1-one,
1-[4-(4-fluorophenyl)phenyl]-3-(2-thienyl)-2-propyn-1-one,
1-[4-(4-methylphenyl)phenyl]-3-(2-thienyl)-2-propyn-1-one,
1-(2,4-dichlorophenyl)-3-(2-thienyl)-2-propyn-1-one,
1-(3,4-dichlorophenyl)-3-(2-thienyl)-2-propyn-1-one,
1-(3,5-dichlorophenyl)-3-(2-thienyl)-2-propyn-1-one,
1-(2,6-difluorophenyl)-3-(2-thienyl)-2-propyn-1-one,
1-(2,4-difluorophenyl)-3-(2-thienyl)-2-propyn-1-one,
1-(3,4-difluorophenyl)-3-(2-thienyl)-2-propyn-1-one,
1-(2,4,6-trifluorophenyl)-3-(2-thienyl)-2-propyn-1-one,
1-(2,4,6-trichlorophenyl)-3-(2-thienyl)-2-propyn-1-one, and
1-(2,6-difluoro-4-trifluoromethylphenyl)-3-(2-thienyl)-2-propyn-1-one.

Within the scope of the compound of formula (IV) used as a starting material in the above-described preparation method (b), a compound in which $R^1$ is para-chloro, namely 1-(4-chlorophenyl)-3-(2-thienyl)-1,3-propanedione, is a well-known compound which is disclosed, for example, in J. Amer. Chem. Soc., Vol. 72, 5219 (1950). However, the compounds of formula (IV) may generally be prepared by the preparation method (i) described below.

Preparation Method (i)

A method which comprises reacting a compound of the formula

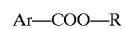

Ar—COO—R    (XV)

wherein Ar is

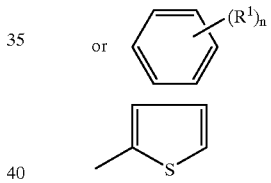

R is $C_{1-6}$ alkyl, and $R^1$ and n are as defined above, with a compound of the formula (XVI)

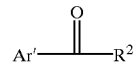

Ar'—C(=O)—R² wherein Ar is

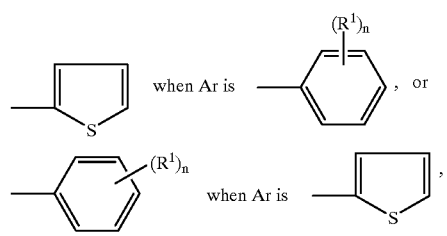

and $R^1$, $R^2$ and n are as defined above.

The above-described method (i) for preparing the compounds of formula (IV) may be carried out according to the procedure described in Organic Synthesis Collective Vol. III, 251.

In the above-described preparation method (i), formula (XV) represent the formula

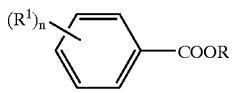
(XV-a)

wherein R, R¹ and n are as defined above, or

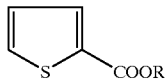
(XV-b)

wherein R is as defined above, and formula (XVI) represents the formula

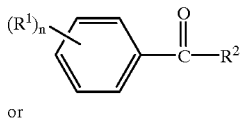
(XVI-a)

or

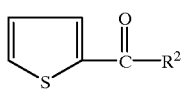
(XVI-b)

These compounds of formulae (XV-a), (XV-b), (XVI-a) and (XVI-b) are compounds which are well known in the field of organic chemistry, and may readily be prepared by any well-known method.

Typical examples of the compounds of the above formula (IV) are as follows:

1-(2-Fluorophenyl)-3-(2-thienyl)-1,3-propanedione,
1-(2-chlorophenyl)-3-(2-thienyl)-1,3-propanedione,
1-(2-trifluoromethylphenyl)-3-(2-thienyl)-1,3-propanedione,
1-(3-chlorophenyl)-3-(2-thienyl)-1,3-propanedione,
1-(3-methylphenyl)-3-(2-thienyl)-1,3-propanedione,
1-(4-fluorophenyl)-3-(2-thienyl)-1,3-propanedione,
1-(4-bromophenyl)-3-(2-thienyl)-1,3-propanedione,
1-(4-iodophenyl)-3-(2-thienyl)-1,3-propanedione,
1-(4-methylphenyl)-3-(2-thienyl)-1,3-propanedione,
1-(4-ethylphenyl)-3-(2-thienyl)-1,3-propanedione,
1-(4-propylphenyl)-3-(2-thienyl)-1,3-propanedione,
1-(4-isopropylphenyl)-3-(2-thienyl)-1,3-propanedione,
1-(4-butylphenyl)-3-(2-thienyl)-1,3-propanedione,
1-(4-tert-butylphenyl)-3-(2-thienyl)-1,3-prop anedione,
1-(4-trifluoromethylphenyl)-3-(2-thienyl)-1,3-propanedione,
1-(4-ethoxyphenyl)-3-(2-thienyl)-1,3-propanedione,
1-(4-propoxyphenyl)-3-(2-thienyl)-1,3-propanedione,
1-(4-methylmercaptophenyl)-3-(2-thienyl)-1,3-propanedione,
1-(4-allyloxyphenyl)-3-(2-thienyl)-1,3-propanedione,
1-(4-propargyloxyphenyl)-3-(2-thienyl)-1,3-propanedione,
1-(4-methoxymethylphenyl)-3-(2-thienyl)-1,3-propanedione,
1-(4-ethoxymethylphenyl)-3-(2-thienyl)-1,3-propanedione,
1-(4-methylmercaptomethylphenyl)-3-(2-thienyl)-1,3-propanedione,
1-(4-difluoromethoxyphenyl)-3-(2-thienyl)-1,3-propanedione,
1-(4- trifluoromethoxyphenyl)-3-(2-thienyl)-1,3-propanedione,
1-[4-(2,2,2-trifluoroethoxy)phenyl]-3-(2-thienyl)-1,3-propanedione,
1-[4-(2,2,3,3-tetrafluoropropyloxy)phenyl]-3-(2-thienyl) 1,3propanedione,
1-(4-methoxymethoxyphenyl)-3-(2-thienyl)-1,3-propanedione,
1-(4-hydroxyphenyl)-3-(2-thienyl)-1,3-propanedione,
1-(4-phenylphenyl)-3-(2-thienyl)-1,3-propanedione,
1-[4-(4-fluorophenyl)phenyl]-3-(2-thienyl)-1,3-propanedione,
1-[4-(4-methylphenyl)phenyl]-3-(2-thienyl)-1,3-propanedione,
1-(2,4-dichlorophenyl)-3-(2-thienyl)-1,3-propanedione,
1-(3,4-dichlorophenyl)-3-(2-thienyl)-1,3-propanedione,
1-(3,5-dichlorophenyl)-3-(2-thienyl)-1,3-propanedione,
1-(2,6-difluorophenyl)-3-(2-thienyl)-1,3-propanedione,
1-(2,4-difluorophenyl)-3-(2-thienyl)-1,3-propanedione,
1-(3,4-difluorophenyl)-3-(2-thienyl)-1,3-propanedione,
1-(2,4,6-trifluorophenyl)-3-(2-thienyl)-1,3-propanedione,
1-(2,4,6-trichlorophenyl)-3-(2-thienyl)-1,3-propanedione,
1-(2,6-difluoro-4-trifluoromethylphenyl)-3-(2-thienyl)-1,3-propanedione,
1-(4-chlorophenyl)-2-fluoro-3-(2-thienyl)-1,3-propanedione,
1-(4-fluorophenyl)-2-methyl-3-(2-thienyl)-1,3-propanedione,
1-(4-chlorophenyl)-2-methyl-3-(2-thienyl)-1,3-propanedione,
1-(4-chlorophenyl)-2-methyl-3-(2-thienyl)-1,3-propanedione,
1-(4-chlorophenyl)-2-ethyl-3-(2-thienyl)-1,3-propanedione,
1-(4-chlorophenyl)-2-propyl-3-(2-thienyl)-1,3-propanedione,
1-(4-chlorophenyl)-2-methoxymethyl-3-(2-thienyl)-1,3-propanedione,
1-(4-chlorophenyl)-2-methylmercaptomethyl-3thienyl)1,3propanedione,
1-(4-chlorophenyl)-2-methylsulinylmethyl-3-(2-thienyl1,3 propanedione,
1-(4-chlorophenyl)-2-methylsulfonylmethyl-3-(2thienyl) 1,3propanedione,
1-(4-chlorophenyl)-2-(2,2,2-trifluoroethyl)-3-(2-thienyl)-1,3-propanedione, and
1-(4-chlorophenyl)-2-(2,2,3,3-tetrafluoropropyl)-3-(2-thienyl)- 1, 3-propanedione.

Within the scope of the compound of formula (IV) used as a starting material in the above-described preparation method (b), the compounds of the formula

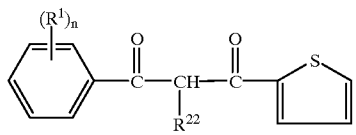

(IV-a)

wherein R¹ and n are as defined above, and R²² represents $C_{1-5}$ alkyl, $C_{2-6}$ (total carbon number) alkoxyalkyl, $C_{2-6}$ (total carbon number) alkylthioalkyl, $C_{2-6}$ (total carbon number) alkylsulfinylalkyl, $C_{2-6}$ (total carbon number) alkylsulfonylalkyl or $C_{1-5}$ haloalkyl, may also be prepared by the preparation method (j) given below.

Preparation Method (j)

A method which comprises reacting a compound of the formula

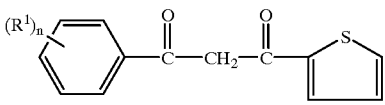

(IV-b)

wherein R¹ and n are as defined above, with a compound of the formula $$R^{22}—X \qquad (XVII)$$

wherein R²² is as defined above, and X is halogen.

The compounds of the above formula (IV-b) may be prepared by the above-described preparation method (i), and the compounds of the above formula (XVII) are compounds which are well known in the field of organic chemistry.

Typical examples of the compounds of the above formula (IV-a) are as follows:

1-(4-Fluorophenyl)-2-methyl-3-(2-thienyl)-1,3-propanedione,
1-(4-chlorophenyl)-2-methyl-3-(2-thienyl)-1,3-propanedione,
1-(4-chlorophenyl)-2-ethyl-3-(2-thienyl)-1,3-propanedione,
1-(4-chlorophenyl)-2-propyl-3-(2-thienyl)-1,3-propanedione,
1-(4-chlorophenyl)-2-methoxymethyl-3-(2-thienyl)-1,3-propanedione,
1-(4-chlorophenyl)-2-methylmercaptomethyl-3-thienyl)1,3propanedione,
1-(4-chlorophenyl)-2-methylsulfinylmethyl-3-(2-thienyl)1,3propanedione,
1-(4-chlorophenyl)-2-methylsulfonylmethyl-3-(2thienyl)1,3propanedione,
1-(4-chlorophenyl)-2-(2,2,2trifluoroethyl)3(2thienyl)1,3propanedione,and
1-(4-chlorophenyl)-2(2,2,3,3tetrafluoropropyl)-3-(2thienyl)1,3propanedione.

In the above-described preparation method (c), the compound of formula (V) used as a starting material comes under the category of the compounds of formula (I) according to the present invention, and typical examples thereof are shown in Table 1 which will be given later.

The compound of formula (IV) used as the other starting material is a compound which is well known in the field of organic chemistry, and may readily be prepared by any conventionally known method.

In the above-described preparation method (d), when R¹ is para-chloro, orthohydroxy or methyl and R² is hydrogen, the compounds of formulae (VIIa) and (VIIb) used as starting materials are well-known compounds which are described, for example, in references such as Indian J. Chem. Sect., B. 32B(11), p1125–9 (1993); J. Indian Chem. Soc., 68(1), p47–51 (1991); and Arch. Pharm., 329(12), 532–534, 1996. Generally, they may be prepared from a chalcone and a hydrazine according to the procedure described in J. Indian Chem. Soc., 64(7), 408 (1987).

The oxidation reaction of the preparation method (d) may be carried out, for example, according to the procedure described in J. Indian Chem. Soc., 64(7), p408 (1987).

Typical examples of the compounds of the above formula (VIIa) are as follows:

3-(2-Fluorophenyl)-5-(2-thienyl)-pyrazoline,
3-(2-chlorophenyl)-5-(2-thienyl)-pyrazoline,
3-(2-trifluoromethylphenyl)-5-(2-thienyl)-pyrazoline,
3-(3-chlorophenyl)-5-(2-thienyl)-pyrazoline,
3-(4-fluorophenyl)-5-(2-thienyl)-pyrazoline,
3-(4-bromophenyl)-5-(2-thienyl)-pyrazoline,
3-(4-iodophenyl)-5-(2-thienyl)-pyrazoline,
3-(4-ethylphenyl)-5-(2-thienyl)-pyrazoline,
3-(4-propylphenyl)-5-(2-thienyl)-pyrazoline,
3-(4-isopropylphenyl)-5-(2-thienyl)-pyrazoline,
3-(4-butylphenyl)-5-(2-thienyl)-pyrazoline,
3-(4-tert-butylphenyl)-5-(2-thienyl)-pyrazoline,
3-(4-trifluoromethylphenyl)-5-(2-thienyl)-pyrazoline,
3-(4-ethoxyphenyl)-5-(2-thienyl)-pyrazoline,
3-(4-propoxyphenyl)-5-(2-thienyl)-pyrazoline,
3-(4-methylmercaptophenyl)-5-(2-thienyl)-pyrazoline,
3-(4-allyloxyphenyl)-5-(2-thienyl)-pyrazoline,
3-(4-propargyloxyphenyl)-5-(2-thienyl)-pyrazoline,
3-(4-methoxymethylphenyl)-5-(2-thienyl)-pyrazoline,
3-(4-ethoxymethylphenyl)-5-(2-thienyl)-pyrazoline,
3-(4-methylmercaptomethylphenyl)-5-(2-thienyl)-pyrazoline,
3-(4-difluoromethoxyphenyl)-5-(2-thienyl)-pyrazoline,
3-(4-trifluoromethoxyphenyl)-5-(2-thienyl)-pyrazoline,
3-[4-(2,2,2-trifluoroethoxy)phenyl]-5-(2-thienyl)-pyrazoline,
3-[4-(2,2,3,3-tetrafluoropropyloxy)phenyl]-5-(2-thienyl)-pyrazoline,
3-(4-methoxymethoxyphenyl)-5-(2-thienyl)-pyrazoline,
3-(4-hydroxyphenyl)-5-(2-thienyl)-pyrazoline,
3-(4-phenylphenyl)-5-(2-thienyl)-pyrazoline,
3-[4-(4-fluorophenyl)phenyl]-5-(2-thienyl)-pyrazoline,
3-[4-(4-methylphenyl)phenyl]-5-(2-thienyl)-pyrazoline,
3-(2,4-dichlorophenyl)-5-(2-thienyl)-pyrazoline,
3-(3,4-dichlorophenyl)-5-(2-thienyl)-pyrazoline,
3-(3,5-dichlorophenyl)-5-(2-thienyl)-pyrazoline,
3-(2,6-difluorophenyl)-5-(2-thienyl)-pyrazoline,
3-(2,4-difluorophenyl)-5-(2-thienyl)-pyrazoline,
3-(3,4-difluorophenyl)-5-(2-thienyl)-pyrazoline,
3-(2,4,6-trifluorophenyl)-5-(2-thienyl)-pyrazoline,
3-(2,4,6-trichlorophenyl)-5-(2-thienyl)-pyrazoline,
3-(2,6-difluoro-4-trifluoromethylphenyl)-5-(2-thienyl)-pyrazoline, 3-(4-chlorophenyl)-4-fluoro-5-(2-thienyl)-pyrazoline,
3-(4-fluorophenyl)-4-methyl-5-(2-thienyl)-pyrazoline,
3-(4-chlorophenyl)-4-methyl-5-(2-thienyl)-pyrazoline,
3-(4-chlorophenyl)-4-ethyl-5-(2-thienyl)-pyrazoline,
3-(4-chlorophenyl)-4-propyl-5-(2-thienyl)-pyrazoline,
3-(4-chlorophenyl)-4-methoxymethyl-5-(2-thienyl)-pyrazoline,
3-(4-chlorophenyl)-4-methylmercaptomethyl-5-(2-thienyl)-pyrazoline,
3-(4-chlorophenyl)-4-methylsulfinylmethyl-5-(2-thienyl)-pyrazoline,
3-(4-chlorophenyl)-4-methylsulfonylmethyl-5-(2-thienyl)-pyrazoline,
3-(4-chlorophenyl)-4-(2,2,2-trifluoroethyl)-5-(2-thienyl)-pyrazoline,
3-(4-chlorophenyl)-4-(2,2,3,3-tetrafluoropropyl)-5-(2-thienyl)-pyrazoline,
1-methyl-3-(4-chlorophenyl)-5-(2-thienyl)-pyrazoline,
1-[3-(4-fluorophenyl)-5-(2-thienyl)-4,5-dihydro-1H-pyrazolyl]-1ethanone,
1-[3-(4-chlorophenyl)-5-(2-thienyl)-4,5-dihydro-1H-pyrazolyl]-1ethanone,
1-[3-(4-chlorophenyl)-5-(2-thienyl)-4,5-dihydro-1Hpyrazolyl]1propanone,
1-[3-(4-chlorophenyl)-5-(2-thienyl)-4,5-dihydro-1H-pyrazolyl]-1butanone,
1[3(4chlorophenyl)5(2thienyl)4,5dihydro1Hpyrazolyl]2methyl1propanoe,
1-[3-(4-chlorophenyl)-5-(2-thienyl)-4,5-dihydro-1Hpyrazolyl]1pentanone,
1[3(4chlorophenyl)5(2thienyl)4,5dihydro1Hpyrazolyl]2,2dimethyl1prope,
1-[3-(4-chlorophenyl)-5-(2-thienyl)-4,5-dihydro-1H-pyrazolyl]-1-none,
1-[3-(4-chlorophenyl)-5-(2-thienyl)-4,5-dihydro-1Hpyrazolyl]2buten1one,
1[3(4chlorophenyl)5(2thienyl)4,5dihydro1Hpyrazolyl](cyclopropyl)methanone,
1-[3-(4-chlorophenyl)-5-(2-thienyl)-4,5-dihydro-1H-pyrazolyl](2,2-difluorocyclopropyl) methanone,
1-[3-(4-chlorophenyl)-5-(2-thienyl)-4,5-dihydro-1H-pyrazolyl] ]-2-methoxy-1-ethanone,
1[3(4chlorophenyl)5(2thienyl)4,5dihydro1Hpyrazolyl]2(methylmercapto)-1-ethanone,
1[3(4chlorophenyl)5(2thienyl)4,5dihydro1Hpyrazolyl](phenyl)methanon,
1[3(4chlorophenyl)5(2thienyl)4,5dihydro1Hpyrazolyl](4fluorophenyl)methanone,
1[3(4chlorophenyl)5(2thienyl)4,5dihydro 1Hpyrazolyl](4trifluoromethylphenyl)methanone,
1-ethylcarbamoyl-3-(4-chlorophenyl)-5-(2-thienyl)-4,5-dihydro-1H-pyrazole,
1-(4-chlorophenyl)carbamoyl-3-(4-chlorophenyl)-5-(2-thienyl)4,5dihydro-1H-pyrazole,
1-ethoxycarbonyl-3-(4-chlorophenyl)-5-(2-thienyl)-4,5-dihydro-1H-pyrazole, and
1-t-butoxycarbonyl-3-(4-chlorophenyl)-5-(2-thienyl)-4,5-dihydro-1H-pyrazole.

Typical examples of the compounds of the above formula (VIIb) are as follows:
5-(2-Fluorophenyl)-3-(2-thienyl)-pyrazoline,
5-(2-chlorophenyl)-3-(2-thienyl)-pyrazoline,
5-(2-trifluoromethylphenyl)-3-(2-thienyl)-pyrazoline,
5-(3-chlorophenyl)-3-(2-thienyl)-pyrazoline,
5-(4-fluorophenyl)-3-(2-thienyl)-pyrazoline,
5-(4-bromophenyl)-3-(2-thienyl)-pyrazoline,
5-(4-iodophenyl)-3-(2-thienyl)-pyrazoline,
5-(4-ethylphenyl)-3-(2-thienyl)-pyrazoline,
5-(4-propylphenyl)-3-(2-thienyl)-pyrazoline,
5-(4-isopropylphenyl)-3-(2-thienyl)-pyrazoline,
5-(4-butylphenyl)-3-(2-thienyl)-pyrazoline,
5-(4-tert-butylphenyl)-3-(2-thienyl)-pyrazoline,
5-(4-trifluoromethylphenyl)-3-(2-thienyl)-pyrazoline,
5-(4-ethoxyphenyl)-3-(2-thienyl)-pyrazoline,
5-(4-propoxyphenyl)-3-(2-thienyl)-pyrazoline,
5-(4-methylmercaptophenyl)-3-(2-thienyl)-pyrazoline,
5-(4-allyloxyphenyl)-3-(2-thienyl)-pyrazoline,
5-(4-propargyloxyphenyl)-3-(2-thienyl)-pyrazoline,
5-(4-methoxymethylphenyl)-3-(2-thienyl)-pyrazoline,
5-(4-ethoxymethylphenyl)-3-(2-thienyl)-pyrazoline,
5-(4-methylmercaptomethylphenyl)-3-(2-thienyl)-pyrazoline,
5-(4-difluoromethoxyphenyl)-3-(2-thienyl)-pyrazoline,
5-(4-trifluoromethoxyphenyl)-3-(2-thienyl)-pyrazoline,
5-[4-(2,2,2-trifluoroethoxy)phenyl]-3-(2-thienyl)-pyrazoline,
5-[4-(2,2,3,3-tetrafluoropropyloxy)phenyl]-3-(2-thienyl)-pyrazoline,
5-(4-methoxymethoxyphenyl)-3-(2-thienyl )-pyrazoline,
5-(4-hydroxyphenyl)-3-(2-thienyl)-pyrazoline,
5-(4-phenylphenyl)-3-(2-thienyl)-pyrazoline,
5-[4-(4-fluorophenyl)phenyl]-3-(2-thienyl)-pyrazoline,
5-[4-(4-methylphenyl)phenyl]-3-(2-thienyl)-pyrazoline,
5-(2,4-dichlorophenyl)-3-(2-thienyl)-pyrazoline,
5-(3,4-dichlorophenyl)-3-(2- thienyl)-pyrazoline,
5-(3,5-dichlorophenyl)-3-(2-thienyl)-pyrazoline,
5-(2,6-difluorophenyl)-3-(2-thienyl)-pyrazoline,
5-(2,4-difluorophenyl)-3-(2-thienyl)-pyrazoline,
5-(3,4-difluorophenyl)-3-(2-thienyl)-pyrazoline,
5-(2,4,6-trifluorophenyl)-3-(2-thienyl)-pyrazoline,
5-(2,4,6-trichlorophenyl)-3-(2-thienyl)-pyrazoline,
5-(2,6-difluoro-4-trifluoromethylphenyl)-3-(2-thienyl)-pyrazoline,
5-(4-chlorophenyl)-4-fluoro-3-(2-thienyl)-pyrazoline,
5-(4-fluorophenyl)-4-methyl-3-(2-thienyl)-pyrazoline,
5-(4-chlorophenyl)-4-methyl-3-(2-thienyl)-pyrazoline,
5-(4-chlorophenyl)-4-ethyl-3-(2-thienyl)-pyrazoline,
5-(4-chlorophenyl)-4-propyl-3-(2-thienyl)-pyrazoline,
5-(4-chlorophenyl)-4-methoxymethyl-3-(2-thienyl)-pyrazoline,
5-(4-chlorophenyl)-4-methylmercaptomethyl-3-(2-thienyl)-pyrazoline,
5-(4-chlorophenyl)-4-methylsulfinylmethyl-3-(2-thienyl)-pyrazoline,
5-(4-chlorophenyl)-4-methylsulfonylmethyl-3-(2-thienyl)-pyrazoline,
5-(4-chlorophenyl)-4-(2,2,2-trifluoroethyl)-3-(2-thienyl)-pyrazoline,
5-(4-chlorophenyl)-4-(2,2,3,3-tetrafluoropropyl)-3-(2-thienyl)-pyrazoline, 1-methyl-5-(4-chlorophenyl)-3-(2-thienyl)-pyrazoline,
1-[5-(4-fluorophenyl)-3-(2-thienyl)-4,5-dihydro-1H-pyrazolyl]-1ethanone,
1-[5-(4-chlorophenyl)-3-(2-thienyl)-4,5-dihydro-1H-pyrazolyl]-1ethanone,
1-[5-(4-chlorophenyl)-3-(2-thienyl)-4,5-dihydro-1Hpyrazolyl]1propanone,
1-[5-(4-chlorophenyl)-3-(2-thienyl)-4,5-dihydro-1H-pyrazolyl]-1butanone,
1[5(4chlorophenyl)3(2thienyl)4,5dihydro1Hpyrazoly]2methyl1propanoe,
1-[5-(4-chlorophenyl)-3-(2-thienyl)-4,5-dihydro-1Hpyrazolyl]1pentanone,
1-[5-(4-chlorophenyl)-3-(2-thienyl)-4,5-dihydro-1Hpyrazolyl]2,2dimethyl-1-propanone,
1-[5-(4-chlorophenyl)-3-(2-thienyl)-4,5-dihydro-1H-pyrazolyl]1hexanone,
1-[5-(4-chlorophenyl)-3-(2-thienyl)-4,5-dihydro-1H-pyrazolyl]-2-buten-1-one,
1[5(4chlorophenyl)3(2thienyl)4,5dihydro1Hpyrazoyl](cyclopropyl)-methanone,
1[5(4chlorophenyl)3(2thienyl)4,5dihydro1Hpyrazoyl](2,2difluorocyclopropyl)methanone,
1-[5-(4-chlorophenyl)-3-(2-thienyl)-4,5-dihydro-1H-pyrazolyl) ]-2-methoxy-1-ethanone,
1[5(4chlorophenyl)3(2thienyl)4,5dihydro1Hpyrazolyl]2methylmercapto1-ethanone,
1[5(4chlorophenyl)3(2thienyl)4,5dihydro1Hpyrazolyl](phenyl)methanone
1[5(4chlorophenyl)3(2thienyl)4,5dihydro1Hpyrazolyl](4fluorophenyl) methanone,
1-[5-(4-chlorophenyl)-3-(2-thienyl)-4,5-dihydro-1H-pyrazolyl](4-trifluoromethylphenyl)methanone,
1-ethylcarbamoyl-5-(4-chlorophenyl)-3-(2-thienyl)-pyrazoline,
1-(4-chlorophenyl)carbamoyl-5-(4-chlorophenyl)-3-(2-thienyl)pyrazoline,
1-ethoxycarbonyl-5-(4-chlorophenyl)-3-(2-thienyl)-pyrazoline, and
1-t-butoxycarbonyl-5-(4-chlorophenyl)-3-(2-thienyl)-pyrazoline.

The compound of formula (VIII) used as the starting material in the above-described preparation method (e) may be prepared by the preparation method (a), (b), (c) or (d).

A typical example of the compound of the above formula (VIII) is as follows:

3-(4-Chlorophenyl)-4-methylmercaptomethyl-5-(2-thienyl)-1H-pyrazole.

Typical examples of the compounds of the above formula (IX) which are obtained by oxidizing a compound of the above formula (VIII) are as follows:

3-(4-Chlorophenyl)-4-methylsulfinylmethyl-5-(2-thienyl)-1H-pyrazole, and
3-(4-chlorophenyl)-4-methylsulfonylmethyl-5-(2-thienyl)-1H-pyrazole.

As described previously, all of the compounds of formulae (II), (IV), (X) and (XI) used as starting materials in the above-described preparation methods (a), (b), (f) and (g) are novel compounds. These compounds, which are novel intermediates according to the present invention, can be represented by the following formula:

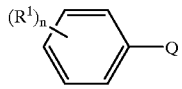

(XVIII)

wherein Q is

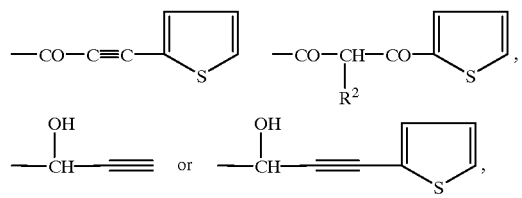

and, $R^1$, $R^2$ and n are as defined above, with the exception of the cases in which Q is

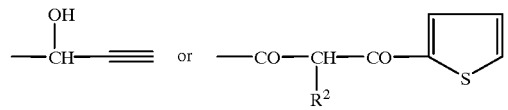

and $R^1$ is para-chloro.

Moreover, the compounds of formulae (VIIa) and (VIIb) used as starting materials in the above-described preparation methods (d) are novel compounds, with the exception of the cases in which $R^1$ is para-chloro, ortho-hydroxy or methyl and $R^2$ is hydrogen. These compounds, which are novel intermediates according to the present invention, can be represented by the following formula:

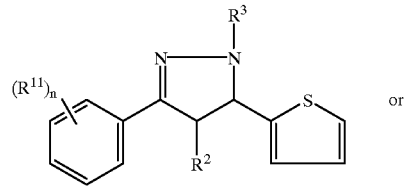

(XIX-a)

or

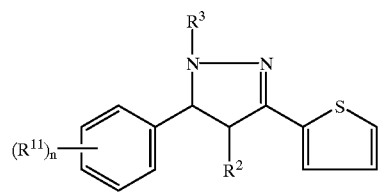

(XIX-b)

wherein $R^{11}$ represents halogen, $C_{1-6}$ alkyl, $C_{1-5}$ haloalkyl, $C_{2-6}$ alkoxy, $C_{1-4}$ alkylthio, $C_{2-5}$ alkenyloxy, $C_{3-5}$ alkynyloxy, $C_{2-6}$ (total carbon number) alkoxyalkyl, $C_{2-6}$ (total carbon number) alkylthioalkyl, $C_{1-5}$ haloalkoxy, $C_{2-6}$ (total carbon number) alkoxyalkoxy, hydroxy or optionally substituted phenyl, and $R^2$, $R^3$ and n are as defined above, with the exception of the cases in which $R^1$ is para-chloro, ortho-hydroxy or methyl and $R^2$ is hydrogen.

The reaction of the above-described preparation method (a) may be carried out in a suitable diluent. Examples of the diluents which may be used for this purpose include water; aliphatic, alicyclic and aromatic hydrocarbons (which may optionally be chlorinated) such as pentane, hexane, cyclohexane, petroleum ether, ligroine, benzene, toluene, xylene, dichloromethane, chloroform, carbon tetrachloride, 1,2-dichloroethane, chlorobenzene and dichlorobenzene; ethers such as ethyl ether, methyl ethyl ether, isopropyl ether, butyl ether, dioxane, dimethoxyethane (DME), tetrahydrofuran (THF) and diethylene glycol dimethyl ether (DGM); nitrites such as acetonitrile, propionitrile and acrylonitrile; alcohols such as methanol, ethanol, isopropanol, butanol and ethylene glycol; and acid amides such as dimethylformamide (DMF), dimethylacetamide (DMA), N-methylpyrrolidone, 1,3-dimethyl-2-imidazolidinone and hexamethylphosphoric triamide (HMPA).

The reaction of the preparation method (a) may be carried out in the presence of an acid catalyst. Examples of the acid catalysts which may be used for this purpose include mineral acids such as hydrochloric acid, sulfuric acid, nitric acid, hydrobromic acid and sodium hydrogen sulfite; organic acids such as formic acid, acetic acid, trifluoroacetic acid, propionic acid, methanesulfonic acid, benzenesulfonic acid and p-toluenesulfonic acid; organic amine hydrochlorides such as pyridine hydrochloride and triethylamine hydrochloride; amine sulfonates such as pyridine p-toluenesulfonate and triethylamine sulfonate.

Although the preparation method (a) may be carried out within a substantially wide temperature range, it is generally suitable to employ a temperature in the range of about −20 to about 150 and preferably about 20 to about 120. Moreover, the reaction should desirably be carried out under atmospheric pressure, but it may optionally be operated under an elevated or reduced pressure.

In carrying out the preparation method (a), the desired compound can be obtained, for example, by reacting a 1 mole of the compound of formula (II) with 1 to 5 moles of the compound of formula (III) in a diluent such as ethanol and in the presence of pyridine p-toluenesul fonate.

The reaction of the above-described preparation method (b) may be carried out in a suitable diluent. Examples of the diluents which may be used for this purpose include water; aliphatic, alicyclic and aromatic hydrocarbons (which may optionally be chlorinated) such as pentane, hexane, cyclohexane, petroleum ether, ligroine, benzene, toluene, xylene, dichloromethane, chloroform, carbon tetrachloride, 1,2-dichloroethane, chlorobenzene and dichlorobenzene; ethers such as ethyl ether, methyl ethyl ether, isopropyl ether, butyl ether, dioxane, dimethoxyethane (DME), tetrahydrofuran (THF) and diethylene glycol dimethyl ether (DGM); nitrites such as acetonitrile, propionitrile and acrylonitrile; alcohols such as methanol, ethanol, isopropanol, butanol and ethylene glycol; and acid amides such as dimethylformamide (DMF), dimethylacetamide (DMA), N-methylpyrrolidone, 1,3-dimethyl-2-imidazolidinone and hexamethylphosphoric triamide (HMPA).

The reaction of the preparation method (b) may be carried out in the presence of an acid catalyst. Examples of the acid catalysts which may be used for this purpose include mineral acids such as hydrochloric acid, sulfuric acid, nitric acid, hydrobromic acid and sodium hydrogen sulfite; organic acids such as formic acid, acetic acid, trifluoroacetic acid, propionic acid, methanesulfonic acid, benzenesulfonic acid and p-toluenesulfonic acid; organic amine hydrochlorides such as pyridine hydrochloride and triethylamine hydrochloride; amine sulfonates such as pyridine p-toluenesulfonate and triethylamine sulfonate.

Although the preparation method (b) may be carried out within a substantially wide temperature range, it is generally suitable to employ a temperature in the range of about −20 to about 150 and preferably about 20 to about 120. Moreover, the reaction should desirably be carried out under atmospheric pressure, but it may optionally be operated under an elevated or reduced pressure.

In carrying out the preparation method (b), the desired compound can be obtained, for example, by reacting a 1 mole of the compound of formula (IV) with 1 to 5 moles of the compound of formula (III) in a diluent such as ethanol and in the presence of pyridine p-toluenesulfonate.

The reaction of the above-described preparation method (c) may be carried out in a suitable diluent. Examples of the diluents which may be used for this purpose include aliphatic, alicyclic and aromatic hydrocarbons (which may optionally be chlorinated) such as pentane, hexane, cyclohexane, petroleum ether, ligroine, benzene, toluene, xylene, dichloromethane, chloroform, carbon tetrachloride, 1,2-dichloroethane, chlorobenzene and dichlorobenzene; ethers such as ethyl ether, methyl ethyl ether, isopropyl ether, butyl ether, dioxane, dimethoxyethane (DME), tetrahydrofuran (THF) and diethylene glycol dimethyl ether (DGM); nitriles such as acetonitrile, propionitrile and acrylonitrile; alcohols such as methanol, ethanol, isopropanol, butanol and ethylene glycol; esters such as ethyl acetate and amyl acetate; acid amides such as dimethylformamide (DMF), dimethylacetamide (DMA), N-methylpyrrolidone, 1,3-dimethyl-2-imidazolidinone and hexamethylphosphoric triamide (HMPA); and sulfones and sulfoxides such as dimethyl sulfoxide (DMSO) and sulfolane.

The reaction of the preparation method (c) may be carried out in the presence of an acid binding agent. Examples of the acid binding agents which may be used for this purpose include inorganic bases, i.e. hydrides, hydroxides, carbonates and bicarbonates of alkali metals and alkaline earth metals, such as sodium hydride, lithium hydride, sodium hydrogen carbonate, potassium hydrogen carbonate, sodium carbonate, potassium carbonate, lithium hydroxide, sodium hydroxide, potassium hydroxide and calcium hydroxide; and organic bases, i.e. alcoholates, tertiary amines, dialkylaminoanilines and pyridines, such as triethylamine, 1,1,4,4-tetramethylethylene-diamine (TMEDA), N,N-dimethylaniline, N,N-diethylaniline, pyridine, 4-dimethylaminopyridine (DMAP),1,4-diazabicyclo [2.2.2] octane (DABCO) and 1,8-diazabicyclo [5.4.0] undec-7-ene (DBU).

Although the preparation method (c) may be carried out within a substantially wide temperature range, it is generally suitable to employ a temperature in the range of about −50 to about 150 and preferably about −20 to about 100. Moreover, the reaction should desirably be carried out under atmospheric pressure, but it may optionally be operated under an elevated or reduced pressure.

In carrying out the preparation method (c), the desired compound can be obtained, for example, by reacting a 1 mole of the compound of formula (V) with 1 to 5 moles of the compound of formula (VI) in a diluent such as tetrahydrofuran and in the presence of sodium hydride.

The reaction of the above-described preparation method (d) may be carried out in a suitable diluent. Examples of the diluents which may be used for this purpose include aliphatic, alicyclic and aromatic hydrocarbons (which may optionally be chlorinated) such as pentane, hexane, cyclohexane, petroleum ether, ligroine, benzene, toluene, xylene, dichloromethane, chloroform, carbon tetrachloride, 1,2-dichloroethane, chlorobenzene and dichlorobenzene.

In the preparation method (d), the oxidation of the compound of formula (VIIa) or (VIIb) is carried out in the presence of an oxidizing agent. Usable oxidizing agents include, for example, manganese dioxide, lead oxide, mercury oxide, silver nitrate and lead tetraacetate.

Although the preparation method (d) may be carried out within a substantially wide temperature range, it is generally suitable to employ a temperature in the range of about −20 to about 200 and preferably about 20 to about 150. Moreover, the reaction should desirably be carried out under atmospheric pressure, but it may optionally be operated under an elevated or reduced pressure.

In carrying out the preparation method (d), the desired compound can be obtained, for example, by reacting a 1 mole of the compound of formula (VIIa) or (VIIb) with 3 to 10 moles of an oxidizing agent such as manganese dioxide, in a diluent such as toluene.

The reaction of the above-described preparation method (e) may be carried out in a suitable diluent. Examples of the diluents which may be used for this purpose include water; aliphatic, alicyclic and aromatic hydrocarbons (which may optionally be chlorinated) such as pentane, hexane, cyclohexane, petroleum ether, ligroine, benzene, toluene, xylene, dichloromethane, chloroform, carbon tetrachloride, 1,2-dichloroethane, chlorobenzene and dichlorobenzene; ethers such as ethyl ether, methyl ethyl ether, isopropyl ether, butyl ether, dioxane, dimethoxyethane (DME), tetrahydroftiran (THF) and diethylene glycol dimethyl ether (DGM); and alcohols such as methanol, ethanol, isopropanol, butanol and ethylene glycol.

The oxidizing agents which may be used to oxidize the compound of formula (VIII) in the preparation method (e) include, for example, hydrogen peroxide, sodium periodate and m-chloroperbenzoic acid.

Although the preparation method (e) may be carried out within a substantially wide temperature range, it is generally suitable to employ a temperature in the range of about −50 to about 200 and preferably about −20 to about 100. Moreover, the reaction should desirably be carried out under atmospheric pressure, but it may optionally be operated under an elevated or reduced pressure.

In carrying out the preparation method (e), the desired compound can be obtained, for example, by reacting a 1 mole of the compound of formula (VIII) with 1 to 5 moles of m-chloroperbenzoic acid in a diluent such as dichloromethane.

The reaction of the above-described preparation method (f) may be carried out in a suitable diluent. Examples of the diluents which may be used for this purpose include water; aliphatic, alicyclic and aromatic hydrocarbons (which may optionally be chlorinated) such as pentane, hexane, cyclohexane, petroleum ether, ligroine, benzene, toluene, xylene, dichloromethane, chloroform, carbon tetrachloride, 1,2-dichloroethane, chlorobenzene and dichlorobenzene; ethers such as ethyl ether, methyl ethyl ether, isopropyl ether, butyl ether, dioxane, dimethoxyethane (DME), tetrahydrofuran (THF) and diethylene glycol dimethyl ether (DGM); ketones such as acetone, methyl ethyl ketone (MEK), methyl isopropyl ketone and methyl isobutyl ketone (MIBK); nitriles such as acetonitrile, propionitrile and acrylonitrile; esters such as ethyl acetate and amyl acetate; acid amides such as dimethylformamide (DMF), dimethylacetamide (DMA), N-methylpyrrolidone, 1,3-dimethyl-2-imidazolidinone and hexamethylphosphoric triamide (HMPA); and sulfoxides such as dimethyl sulfoxide (DMSO).

The oxidizing agents which may be used to oxidize the compound of formula (X) in the preparation method (f) include, for example, manganese dioxide, Jones' reagent and pyridinium dichromate (PDC).

Although the preparation method (f) may be carried out within a substantially wide temperature range, it is generally suitable to employ a temperature in the range of about −20 to about 200 and preferably about 0 to about 120. Moreover, the reaction should desirably be carried out under atmospheric pressure, but it may optionally be operated under an elevated or reduced pressure.

In carrying out the preparation method (f), the desired compound can be obtained, for example, by reacting a 1 mole of the compound of formula (X) with 1 to 10 moles of an oxidizing agent (e.g., PDC) in a diluent such as dichloromethane.

The reaction of the above-described preparation method (g) may be carried out in a suitable diluent. Examples of the diluents which may be used for this purpose include water; aliphatic, alicyclic and aromatic hydrocarbons (which may optionally be chlorinated) such as pentane, hexane, cyclohexane, petroleum ether, ligroine, benzene, toluene, xylene, dichloromethane, chloroform, carbon tetrachloride, 1,2-dichloroethane, chlorobenzene and dichlorobenzene; ethers such as ethyl ether, methyl ethyl ether, isopropyl ether, butyl ether, dioxane, dimethoxyethane (DME), tetrahydrofuran (THF) and diethylene glycol dimethyl ether (DGM); alcohols such as methanol, ethanol, isopropanol, butanol and ethylene glycol; and esters such as ethyl acetate and amyl acetate.

The reaction of the preparation method (g) may be carried out in the presence of an acid binding agent. Examples of the acid binding agents which may be used for this purpose include inorganic bases, i.e. hydrides, hydroxides, carbonates and bicarbonates of alkali metals and alkaline earth metals, such as sodium hydride, lithium hydride, sodium hydrogen carbonate, potassium hydrogen carbonate, sodium carbonate, potassium carbonate, lithium hydroxide, sodium hydroxide, potassium hydroxide and calcium hydroxide.

The reaction of the preparation method (g) may be carried out in the presence of a catalyst. Examples of the catalysts which may be used for this purpose include tetrakistriphenylphosphine palladium.

The above-described preparation method (g) may also be carried out by using a phase-transfer catalyst. Examples of the diluents which may be used for this purpose include water; aliphatic, alicyclic and aromatic hydrocarbons (which may optionally be chlorinated) such as pentane, hexane, cyclohexane, petroleum ether, ligroine, benzene, toluene, xylene, dichloromethane, chlorobenzene and dichlorobenzene; and ethers such as ethyl ether, methyl ethyl ether, isopropyl ether, butyl ether, dioxane, dimethoxyethane (DME), tetrahydrofuran (THF) and diethylene glycol dimethyl ether (DGM).

Examples of usable phase-transfer catalysts include quaternary ions such as tetramethylammonium bromide, tetrapropylammonium bromide, tetrabutylammonium bromide, tetrabutylammonium bissulfate, tetrabutylammonium iodide, trioctylmethylammonium chloride, benzyltriethylammonium bromide, butylpyridinium bromide, heptylpyridinium bromide and benzyltriethylammonium chloride; crown ethers such as dibenzo-18-crown-6, dicyclohexyl-18-crown-6 and 18-crown-6; and cryptands such as [2.2.2]-cryptate, [2.1.1]-cryptate, [2.2.1]-cryptate, [2.2. B]-cryptate, [20202S]-cryptate and [3.2.2]-cryptate.

Although the preparation method (g) may be carried out within a substantially wide temperature range, it is generally suitable to employ a temperature in the range of about 0 to about 200. and preferably about 0 to about 120. Moreover, the reaction should desirably be carried out under atmospheric pressure, but it may optionally be operated under an elevated or reduced pressure.

In carrying out the preparation method (g), the desired compound can be obtained, for example, by reacting a 1 mole of the compound of formula (XI) with 1 to 5 moles of the compound of formula (XII) in a diluent such as benzene) and in the presence of tetrakistriphenylphosphine palladium.

The reaction of the above-described preparation method (h) may be carried out in a suitable diluent. Examples of the diluents which may be used for this purpose include aliphatic, alicyclic and aromatic hydrocarbons such as pentane, hexane, cyclohexane, petroleum ether, ligroine, benzene, toluene and xylene; and ethers such as ethyl ether, methyl ethyl ether, isopropyl ether, butyl ether, dioxane, dimethoxyethane (DME), tetrahydrofuran (THF) and diethylene glycol dimethyl ether (DGM).

The reaction of the preparation method (h) may be carried out in the presence of an organometallic reagent. Examples of the organometallic reagents which may be used for this purpose include organolithium compound such as methyllithium, n-butyllithium, sec-butyllithium, tert-butyllithium, phenyllithium, dimetylcopper-lithium, lithium diisopropylamide, lithium cyclohexylisopropylamide, lithium dicyclohexylamide, n-butyllithium DABCO, n-butyllithium DBU and n-butyllithium TMEDA; and organic Grignard reagents such as methylmagnesium bromide, ethylmagnesium iodide and n-propylmagnesium bromide.

Although the preparation method (h) may be carried out within a substantially wide temperature range, it is generally suitable to employ a temperature in the range of about −100 to about 50. and preferably about −80 to about 25. Moreover, the reaction should desirably be carried out under atmospheric pressure, but it may optionally be operated under an elevated or reduced pressure.

In carrying out the preparation method (h), the desired compound can be obtained, for example, by reacting a 1 mole of the compound of formula (XIII) with 1 to 3 moles of the compound of formula (XIV) in a diluent such as tetrahydrofuran and in the presence of n-butyllithium.

The reaction of the above-described preparation method (i) may be carried out in a suitable diluent. Examples of the diluents which may be used for this purpose include aliphatic, alicyclic and aromatic hydrocarbons such as pentane, hexane, cyclohexane, petroleum ether, ligroine, benzene, toluene, xylene; ethers such as ethyl ether, methyl ethyl ether, isopropyl ether, butyl ether, dioxane, dimethoxyethane (DME), tetrahydrofuran (THF) and diethylene glycol dimethyl ether (DGM); alcohols such as methanol, ethanol, isopropanol, butanol and ethylene glycol; and acid amides such as dimethylformamide (DMF), dimethylacetamide (DMA), N-methylpyrrolidone, 1,3-dimethyl-2-imidazolidinone and hexamethylphosphoric triamide (HMPA).

The reaction of the preparation method (i) may be carried out in the presence of an acid binding agent. Examples of the acid binding agents which may be used for this purpose include inorganic bases, i.e. hydrides, hydroxides, carbonates and bicarbonates of alkali metals and alkaline earth metals, such as sodium hydride, lithium hydride, sodium hydrogen carbonate, potassium hydrogen carbonate, sodium carbonate, potassium carbonate, lithium hydroxide, sodium-metal amides such as lithium amide, sodium amide and potassium amide; and hydroxide, potassium hydroxide and calcium hydroxide; inorganic alkali organic bases such as alcoholates.

Although the preparation method (i) may be carried out within a substantially wide temperature range, it is generally suitable to employ a temperature in the range of about −20 to about 200. and preferably about 20 to about 150. Moreover, the reaction should desirably be carried out under atmospheric pressure, but it may optionally be operated under an elevated or reduced pressure.

In carrying out the preparation method (i), the desired compound can be obtained, for exarnple, by reacting a 1 mole of the compound of formula (XV-a) with 1 to 1.5 moles of the compound of formula (XVI-b) in a diluent such as tetrahydrofuran and in the presence of sodium hydride.

The reaction of the above-described preparation method (j) may be carried out in a suitable diluent. Examples of the diluents which may be used for this purpose include water; aliphatic, alicyclic and aromatic hydrocarbons (which may optionally be chlorinated) such as pentane, hexane, cyclohexane, petroleum ether, ligroine, benzene, toluene, xylene, dichloromethane, chloroform, carbon tetrachloride, 1,2-dichloroethane, chlorobenzene and dichlorobenzene; ethers such as ethyl ether, methyl ethyl ether, isopropyl ether, butyl ether, dioxane, dimethoxyethane (DME), tetrahydrofuran (THF) and diethylene glycol dimethyl ether (DGM); ketones such as acetone, methyl ethyl ketone (MEK), methyl isopropyl ketone and methyl isobutyl ketone (MIBK); nitriles such as acetonitrile, propionitrile and acrylonitrile; esters such as ethyl acetate and amyl acetate; acid amides such as dimethylformamide (DMF), dimethylacetamide (DMA), N-methylpyrrolidone, 1,3-dimethyl-2-imidazolidinone and hexamethylphosphoric triamide (HMPA); sulfones and sulfoxides such as dimethyl sulfoxide (DMSO) and sulfolane; and bases such as pyridine.

The reaction of the preparation method (j) may be carried out in the presence of an acid binding agent. Examples of the acid binding agents which may be used for this purpose include inorganic bases, i.e. hydrides, hydroxides, carbonates and bicarbonates of alkali metals and alkaline earth metals, such as sodium hydride, lithium hydride, sodium hydrogen carbonate, potassium hydrogen carbonate, sodium carbonate, potassium carbonate, lithium hydroxide, sodium hydroxide, potassium hydroxide and calcium hydroxide; inorganic alkali metal amides such as lithium amide, sodium amide and potassium amide; organic bases, i.e. alcoholates, tertiary amines, dialkylaminoanilines and pyridines such as triethylamine,1,1,4,4tetramethylethylenediamine (TMEDA), N,N-dimethylaniline, N,N-diethylaniline, pyridine, 4-dimethyl-aminopyridine (DMAP), 1,4-diazabicyclo[2.2.2]octane (DABCO) and 1,8-diazabicyclo-[5.4.0]undec-7-ene (DBU); and organolithium compound such as methyllithium, n-butyllithium, sec-butyllithium, tert-butyllithium, phenyllithium, dimetylcopper-lithium, lithium diisopropylamide, lithium cyclohexylisopropylamide, lithium dicyclohexylamide, n-butyl lithium. DAB CO, n-butyllithium DBU and n-butyllithium TMEDA; and organic Grignard reagents such as methylmagnesium bromide, ethylmagnesium iodide and n-propylmagnesium bromide.

The above-described preparation method (j) may also be carried out by using a phase-transfer catalyst. Examples of the diluents which may be used for this purpose include water; aliphatic, alicyclic and aromatic hydrocarbons (which may optionally be chlorinated) such as pentane, hexane, cyclohexane, petroleum ether, ligroine, benzene, toluene, xylene, dichloromethane, chlorobenzene and dichlorobenzene; and ethers such as ethyl ether, methyl ethyl ether, isopropyl ether, butyl ether, dioxane, dimethoxyethane (DME), tetrahydrofuran (THF) and diethylene glycol dimethyl ether (DGM).

Examples of usable phase-transfer catalysts include quaternary ions such as tetramethylammonium bromide, tetrapropylammonium bromide, tetrabutylammonium bromide, tetrabutylammonium bissulfate, tetrabutylammonium iodide, trioctylmethylammonium chloride, benzyltriethylammonium bromide, butylpyridinium bromide, heptylpyridinium bromide and benzyltriethylammonium chloride; crown ethers such as dibenzo-18-crown-6, dicyclohexyl-18-crown-6 and 18-crown-6; and cryptands such as [2.2.2]-cryptate, [2.1.1]-cryptate, [2.2.1]-cryptate, [2.2. B]-cryptate, [20202S]-cryptate and [3.2.2]-cryptate.

Although the preparation method (j) may be carried out within a substantially wide temperature range, it is generally suitable to employ a temperature in the range of about −50 to about 200 and preferably about −20 to about 100. Moreover, the reaction should desirably be carried out under atmospheric pressure, but it may optionally be operated under an elevated or reduced pressure.

In carrying out the preparation method (j), the desired compound can be obtained, for example, by reacting a 1 mole of the compound of formula (IV-b) with 1 to 5 moles of the compound of formula (XVII) in a diluent such as tetrahydrofuran and in the presence of sodium hydride.

The compounds of formula (I) according to the present invention manifest a powerfill nematicidal action and anthelmintic action. Accordingly, they can be used as nematicides and anthelmintics. Moreover, the active compounds of formula (I) according to the present invention exhibit a proper controlling effect on noxious nematodes without causing phytotoxicity to cultivated plants, and on parasites without causing toxicity to mammals.

Examples of the nematodes to which the compounds of formula (I) according to the present invention, can be applied include as follows, but are not limited thereto; root-lesion nematodes (Pratylenchus spp.), potato cyst nematode (*Globodera rostochiensis* Wollenweber), soybean cyst nematode (*Heterodera glycines* Ichinohe), root-knot nematodes (Meloidogyne spp.), rice heart nematode (*Aphelenchoides besseyi* Christie) and pine nematode (*Bursaphelenchus xylophilus*).

Examples of the parasites to which the compounds of the formula (I) according to the present invention can be applied include as follows, but not limited thereto;

Parasites of cattle and sheep:
    twisted stomach worm (Mecistocirrus spp., Haemonchus spp.)
    stomach worm (Ostertagia spp.)
    esophagus worm (Gongylonema spp.)
    hair worm (Cooperia spp., Nematodirus spp., Trichosrongylus spp.)
    nodular worm (Oesophagostomum spp.)
    hook worm (Bunostomum spp.)
    tape worm (Moniezia spp., Taenia spp.)
    lung worm (Dicyocaulus spp.)
    liver fluke (Fasciola spp.)
    pancreas fluke (Eurytreama spp.)
    fluke (Paramphistomum spp., Fischoederius spp., Gasrtothylax spp.)

Parasites of horse:
    tape worm (Anoplocephala spp., Paranoplocephala spp.)
    strongylida (Strongylus spp., Triodontophorus spp., Oerophagodontus spp.,
    Trichonema spp., Poteriostomum spp., Cylicocyclus spp., Cyliodontophorus spp.)
    filaria (Setaria spp.)
    pin worm (Oxyuris spp.)
    round worm (Parascaris spp.)
    stomach worm (Habronema spp.)

Parasites of swine:
    round worm (Ascaris spp.)
    hook worm (Necator spp , Globocephalus spp.)
    nodular worm (Oesophagostomum spp.)
    trichinell a (Trichinella spp.)
    macracanthorhynchus (Macracanthorhynchus spp.)
    gnathostoma (Gnathostoma spps)
    kidney worm (Stephanurus spp., Dioctohphyme spp.)
    lung worm (Metastrongylus spp., Choerostrongylus spp.)

Parasites of dog:
    round worm (Toxocala spp. Toxascaris spp.)
    hook worm (Uncinaria spp. Ancylostoma spp.)
    whip worm (Trichocephalus spp.)
    thelazia (Thelaza spp.)
    heart worm (Dirofilaria spp.)
    trichinella (Trichinella spp.)
    tape worm (Diphyllobotrium spp., Mesocestoides spp., Taenia spp.,
    Echinococcus spp. Dipyldum spp., Multiceps spp.)
    fluke (Echinocasmus spp., Plagiorchis spp., Hcterophyes spp., Metagonimus spp.)

Parasites of cat:
    round worn (Toxoxala spp.)

Parasites of chicken:
    round worm (Ascaridia spp.)
    hair worm (Capillaria spp.)
    cecal wonn (Heterakis spp.)
    tape worm (Ralletina spp., Hymenolepis spp.)
    fluke (Echinoparyphium spp., Echinostoma spp., Catatropis spp..
    Prosthogonimus spp, Metorchis spp.)
    gape worm (Syngamus spp.)

Parasites of fish:
    monogenea (Gyrodactylus spp., Dactylogyrus spp.)

Parasites of human
    round worm (Ascaris spp.)
    pin worm (Enterobius spp.)
    hook worm (Ancylostama spp., Necator spp.)
    whip worm (Trichocephalus spp.)
    hair worm (Trichostrongylus spp.)
    filaria (Brugia spp., Wuchereria spp., Onchocerca spp.)
    tape worm (Diphyllobothrium spp., Diplogonoporus spp., Taenia spp.,
    Raillietina spp., Taeniarynchus spp.)
    schistosoma (Schistosoma spp.)
    lung fluke (Paragonimus spp.)
    liver fluke (Clonorchis spp.)

The active compounds of formula (I) according to the present invention, in a case where the active compounds are used as nematicides, can be present in their commercially available formulations and in the use forms prepared from these formulations, as a mixture with other active compounds such as insecticides, sterilizing agents, acaricides or fingicides. The aforesaid insecticides include, for example, organic phosphates, carbamates, carboxylates, chlorinated hydrocarbons, chloronicotinyl compounds, and insecticidal substances produced by microorganisms.

The active compounds of formula (I) according to the present invention can further be present in their commercially available formulations and in the use forms prepared from these formulations, as a mixture with synergistic agents. Synergistic agents are compounds which increase the action of the active compounds, without it being necessary for the synergistic agent added to be active itself.

The content of the active compounds of formula (I) according to the present invention in their commercially available use forms can vary within wide limits. The concentration of the active compounds of formula (I) according to the present invention in their use forms can be from 0.000001 to 100% by weight, preferably between 0.00001 to 1% by weight.

The active compounds of the present invention can be converted into customary formulations, such as solution, emulsions, wettable powder, suspension, powder, foam, paste, granule, natural and synthetic materials impregnated with active compounds, microcapsule, coating composition for seeds, and fumigant, liquid, pill, tablet and capsul.

These formulations may be produced in the manner known per se, for example, by mixing an active compound with extenders, i.e. liquid diluents, liquefied gas diluents, solid diluents or carriers, optionally with the use of surface-active agents, i.e. emulsifying agents and/or dispersing agents and/or foam-forming agents. In the case of the use of water as an extender, organic solvents, for example, may be used as auxiliary solvents.

As liquid diluents or carriers, there may be used, for example, aromatic hydrocarbons such as xylene, toluene and alkylnaphthalenes; chlorinated aromatic and chlorinated aliphatic hydrocarbons such as chlorobenzenes, chloroethylenes and methylene chloride; aliphatic hydrocarbons such as cyclohexane and paraffins (for example, mineral oil fractions); alcohols such as butanol, glycol, and their ethers and esters; ketones such as acetone, methyl ethyl ketone, methyl isopropyl ketone and cyclohexanone; strongly polar solvents such as dimethylformamide and dimethyl sulfoxide; as well as water.

By liquefied gaseous diluents or carriers are meant liquids which would be gaseous at normal temperature and normal pressure, for example, aerosol propellants such as butane, propane, nitrogen gas, carbon dioxide and halogenated hydrocarbons.

As solid diluents, there may be used, for example, ground natural minerals such as kaolins, clays, talc, chalk, quartz, attapulgite, montmorillonite and diatomaceous earth; and ground synthetic minerals such as highly-dispersed silicic acid, alumina and silicates.

As solid carriers for granules, there may be used, for example, crushed and fractionated natural rocks suck as calcite, marble, pumice, sepiolite and dolomite; synthetic granules of inorganic or organic meals; and granules of organic materials such as sawdust, coconut shells, maize cobs and tobacco stalks.

As emulsifying and/or foam-forming agents, there are may be used, for example, non-ionic and anionic emulsifiers such as polyoxyethylene-fatty acid esters, polyoxyethylene-fatty alcohol esters (for example, alkylaryl polyglycol ethers, alkylsulfonates, alkylsulfates and arylsulfates) and albumin hydrolysis products. Usable dispersing agents include, for example, lignin sulfite waste liquors and methylcellulose.

Adhesives may also be used in formulations such as powders, granules and emulsions. Usable adhesives include, for example, carboxymethylcellulose, and natural and synthetic polymers such as gum arabic, polyvinyl alcohol and polyvinyl acetate.

It is possible to use colorants including, for example, inorganic pigments (for example, iron oxide, titanium oxide and Prussian Blue); organic dyestuffs such as alizarin dyestuffs, azo dyestuffs and metal phthalocyanine dyestuffs; and trace elements such as salts of iron, manganese, boron, copper, cobalt, molybdenum and zinc.

The formulations can generally contain 0.1 to 95% by weight, preferably 0.5 to 90% by weight, of the aforesaid active compounds.

Now, the preparation and use of compounds in accordance with the present invention are more specifically explained with reference to the following examples. However, it is to be understood that the present invention is not limited thereto. Unless otherwise specified, all parts are by weight.

EXAMPLS

Synthesis Example 1

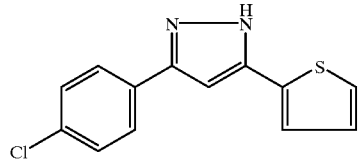

Hydrazine hydrate (228 mg, 4.6 mM) and pyridinium p-toluenesulfonate (50 mg) were added to a solution of 1-(4-chlorophenyl)-3-(2-thienyl)-2-propyn-1-one (750 mg, 3.0 mM) in ethanol (30 ml), and this mixture was heated under reflux for 2 hours. After the mixture was allowed to cool to room temperature, the solvent was distilled off under reduced pressure, and the resulting residue was dissolved in ethyl acetate (50 ml). This solution was washed with a saturated aqueous solution of sodium hydrogen carbonate and a saturated aqueous solution of sodium chloride, and dried over magnesium sulfate. Thereafter, the solvent was distilled off under reduced pressure to obtain 634 mg of 3-(4-chlorophenyl)-5-(2-thienyl)-1H-pyrazole, m.p. 217° C., in an 80% yield.

Synthesis Example 2

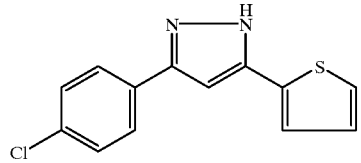

Hydrazine hydrate (6.2 g, 125 mM) was added to a solution of 1-(4-chlorophenyl)-3-(2-thienyl)-1,3-propanedione (22 g, 83 mM) in ethanol (300 ml), and this mixture was heated under reflux for 3 hours. After the mixture was allowed to cool to room temperature, the solvent was distilled off under reduced pressure.

The resulting crystals were washed with a solvent mixture composed of diethyl ether and hexane to obtain 20 g (76 mM) of 3-(4-chlorophenyl)-5-(2-thienyl)-1H-pyrazole, m.p. 217° C., in a 91% yield.

Synthesis Example 3

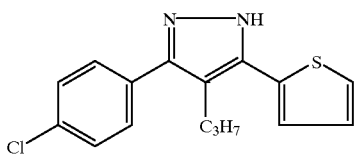

1-(4-Chlorophenyl)-2-propyl-3-(2-thienyl)-1,3-propanedione (1.4 g, 4.6 mM) was dissolved in ethanol (50 ml), and hydrazine hydrate (343 mg, 6.9 mM) was added thereto. This mixture was heated under reflux for 3 hours. After the mixture was allowed to cool, the solvent was distilled off under reduced pressure. The resulting precipitate was filtered while being washed with a solvent mixture composed of hexane and ether to obtain 1.3 g (4.3 mM) of 3-(4-chlorophenyl)-4-propyl-5-(2-thienyl)-1H-pyrazole, m.p. 129–132° C., in a 94% yield.

Synthesis Example 4

Mixture of

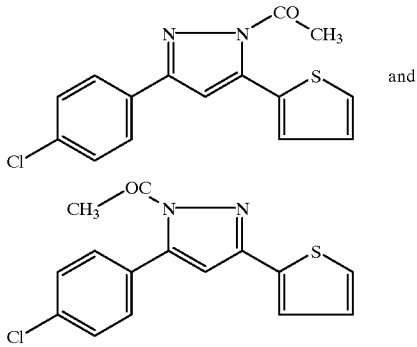

Acetyl chloride (391 mg, 5 mM) and an oil suspension of sodium hydride (230 mg 5.8 mM) were added to a solution of 3-(4-chlorophenyl)-5-(2-thienyl)-1H-pyrazole (1 g, 3.8 mM) in tetrahydrofuran (30 ml), and this mixture was reacted at room temperature for 5 hours. After the reaction was stopped by the addition of water, the reaction mixture was extracted with ethyl acetate. The organic layer was washed with a saturated aqueous solution of sodium chloride and dried over anhydrous sodium sulfate. Thereafter, the solvent was distilled off under reduced pressure, and the resulting residue was purified by column chromatography (SiO₂; hexane/ethyl acetate=10/1 to 5/1) to obtain 1.03 g of an about 1:1 mixture of 1-acetyl-3-(4-chlorophenyl)-5-(2-thienyl)-1H-pyrazole and 1-acetyl-3-(2-thienyl)-5-(4-chlorophenyl)-1H-pyrazole, m.p. 86–89° C.

Synthesis Example 5

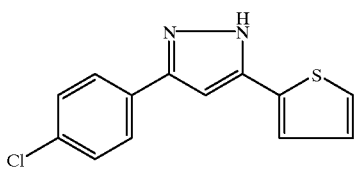

Active manganese dioxide (4.35 g, 50 mM) was added to a solution of 3-(4-chlorophenyl)-5-(2-thienyl)-pyrazoline (2.62 g, 10 mM) in toluene (100 ml). This mixture was heated under reflux for 3 hours, and then filtered while hot. After the filtrate was allowed to cool, the precipitated crystals were collected by filtration, washed with a small volume of cold toluene, and then air-dried to obtain 1.46 g of the desired 3-(4-chlorophenyl)-5-(2-thienyl)-1H-pyrazole, m.p. 217° C., in a 56% yield.

Synthesis Example 6

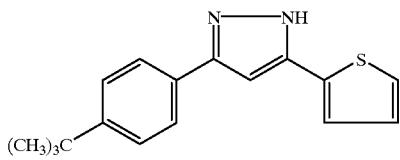

A 60% suspension of sodium hydride (1.5 g, 37 mM) was added to a solution of 4-tert-butylacetophenone (5 g, 28 mM) and ethyl 2-thiophenecarboxylate (4.4 g, 28 mM) in tetrahydrofuran (100 ml), and this mixture was heated under reflux for 3 hours. After the mixture was allowed to cool, 100 ml of water was added thereto. The resulting mixture was adjusted to pH 1 with a concentrated aqueous solution of hydrochloric acid and then extracted with ethyl acetate. The organic layer was washed with a saturated aqueous solution of sodium chloride and dried over anhydrous sodium sulfate. Thereafter, the solvent was distilled off under reduced pressure, and the resulting residue was dissolved in ethanol. Hydrazine hydrate (2.1 g, 43 mM) was added thereto, and this mixture was heated under reflux for 3 hours. After the mixture was allowed to cool, the solvent was distilled off under reduced pressure to obtain 9.1 g of 3-(4-tert-butylphenyl)-5-(2-thienyl)-1H-pyrazole, m.p. 61–65° C.

Synthesis Example 7

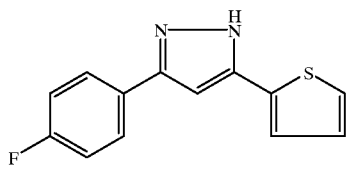

Active manganese dioxide (7.5 g, 86 mM) was added to a solution of 5-(4-fluorophenyl)-3-(2-thienyl)-pyrazoline (3.6 g, 14.6 mM) in toluene (150 ml). This mixture was heated under reflux for 1 hour, and then filtered while hot. The filtrate was concentrated under reduced pressure, and the resulting residue was recrystallized from ethanol to obtain 1.1 g of the desired 3-(4-fluorophenyl)-5-(2-thienyl)-1H-pyrazole, m.p. 181–184° C., in a 30% yield.

The following Table 1 shows compounds of formula (I) which can be prepared in the same manner as described in the foregoing Synthesis Examples 1 to 7, together with the compounds obtained in the foregoing Synthesis Examples 1 to 7.

TABLE 1

| Compound No. | $(R^1)n$ | $R^2$ | $R^3$ | Melting point (m.p.) ° C., $n_D^{20}$ |
|---|---|---|---|---|
| 1 | 2-F | H | H | 163–165 |
| 2 | 2-Cl | H | H | 122–123 |
| 3 | 2-CF$_3$ | H | H | 113–116 |
| 4 | 3-Cl | H | H | 182–183 |
| 5 | 3-CH$_3$ | H | H | 163–165 |
| 6 | 4-F | H | H | 181–184 |
| 7 | 4-Cl | H | H | 217 |
| 8 | 4-Br | H | H | 220–224 |
| 9 | 4-I | H | H | 221–223 |
| 10 | 4-CH$_3$ | H | H | 177–180 |
| 11 | 4-C$_2$H$_5$ | H | H | 170–171 |
| 12 | 4-C$_2$H$_7$-n | H | H | 131–136 |
| 13 | 4-C$_2$H$_7$-i | H | H | |
| 14 | 4-C$_4$H$_9$-n | H | H | 144–147 |
| 15 | 4-C$_4$H$_9$-t | H | H | 61–65 |
| 16 | 4-CF$_3$ | H | H | 233–234 |
| 17 | 4-C$_2$H$_5$O | H | H | 159–166 |
| 18 | 4-C$_3$H$_7$O | H | H | 124–135 |
| 19 | 4-CH$_3$S | H | H | 157–165 |
| 20 | 4-CH$_2$=CHCH$_2$O | H | H | |
| 21 | 4-CHCCH$_2$O | H. | H | |
| 22 | 4-CH$_3$OCH$_2$ | H | H | 111–116 |
| 23 | 4-C$_2$H$_5$OCH$_2$ | H | H | 97–105 |
| 24 | 4-CH$_3$SCH$_2$ | H | H | 110–113 |
| 25 | 4-CHF$_2$O | H | H | 127–131 |
| 26 | 4-CF$_3$O | H | H | 146–151 |
| 27 | 4-CF$_3$CH$_2$O | H | H | 177–181 |
| 28 | 4-CHF$_2$CF$_2$CH$_2$O | H | H | |
| 29 | 4-CH$_3$OCH$_2$O | H | H | 112–114 |
| 30 | 4-OH | H | H | More than 250 |
| 31 | 4-C$_6$H$_5$ | H | *H | |
| 32 | 4-(4-F—C$_6$H$_4$) | H | H | 220–225 |
| 33 | 4-(4-CH$_3$—C$_6$H$_4$) | H | H | |
| 34 | 2,4-Cl$_2$ | H | H | 171–174 |
| 35 | 3,4-Cl$_2$ | H | H | 210–211 |
| 36 | 3,5-Cl$_2$ | H | H | 241–243 |
| 37 | 2,6-F$_2$ | H | H | 133–134 |
| 38 | 2,4-F$_2$ | H | H | 127–130 |
| 39 | 3,4-F$_2$ | H | H | |
| 40 | 2,4,6-F$_3$ | H | H | |
| 41 | 2,4,6-Cl$_3$ | H | H | |
| 42 | 4-CF$_3$,2,6-F$_2$ | H | H | |
| 43 | 4-Cl | F | H | |
| 44 | 4-F | CH$_3$ | H | |
| 45 | 4-Cl | CH$_3$ | H | 194–195 |
| 46 | 4-Cl | C$_2$H$_5$ | H | 133–134 |
| 47 | 4-Cl | C$_2$H$_7$-n | H | 129–132 |
| 48 | 4-Cl | CH$_2$OCH$_3$ | H | |
| 49 | 4-Cl | CH$_2$SCH$_3$ | H | 131–137 |
| 50 | 4-Cl | CH$_2$SOCH$_3$ | H | |
| 51 | 4-Cl | CH$_2$SO$_2$CH$_3$ | H | |
| 52 | 4-Cl | CH$_2$CF$_3$ | H | |
| 53 | 4-Cl | CH$_2$CF$_2$CHF$_2$ | H | |
| 54 | 4-Cl | H | CH$_3$ | 98–103 |
| 55 | 4-Cl | H | C$_2$H$_7$-i | *1) |
| 56 | 4-Cl | H | C$_4$H$_9$-n | *2) |
| 57 | 4-F | H | COCH$_3$ | |
| 58 | 4-Cl | H | COCH$_3$ | 86–89 |
| 59 | 4-Cl | H | COC$_2$H$_5$ | |
| 60 | 4-Cl | H | COC$_3$H$_7$-n | |
| 61 | 4-Cl | H | COC$_3$H$_7$-i | $n_D^{20}$1.6299 |
| 62 | 4-Cl | H | COC$_4$H$_9$-n | |
| 63 | 4-Cl | H | COC$_4$H$_9$-t | $n_D^{20}$1.5979 |
| 64 | 4-Cl | H | COC$_5$H$_{11}$-n | $n_D^{20}$1.5881 |
| 65 | 4-Cl | H | COCH=CH—CH$_3$ | $n_D^{20}$1.6691 |

TABLE 1-continued

Structures (two isomers shown):
- 1-R³, 5-(R¹)n-phenyl, 3-thienyl, 4-R² pyrazole
- 1-R³, 3-(R¹)n-phenyl, 5-thienyl, 4-R² pyrazole

| Compound No. | (R¹)n | R² | R³ | Melting point (m.p.) °C., $n_D^{20}$ |
|---|---|---|---|---|
| 66 | 4-Cl | H | CO—cyclopropyl | $n_D^{20}$ 1.6533 |
| 67 | 4-Cl | H | CO—(2,2-difluorocyclopropyl) | $n_D^{20}$ 1.6320 |
| 68 | 4-Cl | H | COCH$_2$OCH$_3$ | 109–112 |
| 69 | 4-Cl | H | COCH$_2$SCH$_3$ | $n_D^{20}$ 1.6369 |
| 70 | 4-Cl | H | COC$_6$H$_5$ | $n_D^{20}$ 1.6769 |
| 71 | 4-Cl | H | CO—C$_6$H$_4$-4-F | $n_D^{20}$ 1.6623 |
| 72 | 4-Cl | H | CO—C$_6$H$_4$-4-CF$_3$ | 221–225 |
| 73 | 4-Cl | H | CONHC$_2$H$_5$ | 92–95 |
| 74 | 4-Cl | H | CONHC$_6$H$_4$-4-Cl | 139–148 |
| 75 | 4-Cl | H | COOC$_2$H$_5$ | 130–132 |
| 76 | 4-Cl | H | COOC$_4$H$_9$-t | 88–91 |
| 77 | 4-Cl | H | CO—C(CH$_3$)=CH$_2$ | |
| 78 | 4-Cl | Cl | H | 182–185 |
| 79 | 4-Cl | Br | H | 196–199 |
| 80 | 4-Cl | H | COCH$_2$Cl | 108–110 |
| 81 | 4-Cl | H | CH(OC$_2$H$_5$)$_2$ | $n_D^{20}$ 1.5745 |
| 82 | 4-C$_2$H$_5$ | H | COCH$_3$ | $n_D^{20}$ 1.6381 |
| 83 | 4-C$_3$H$_7$-n | H | COCH$_3$ | 3) |
| 84 | 4-I | H | COCH$_3$ | $n_D^{20}$ 1.6986 |
| 85 | 4-F | H | COCH$_3$ | 4) |
| 86 | 4-Cl | H | CH(OCH$_3$)$_2$ | 65–71 |
| 87 | 4-CH$_3$O | Br | COCH$_3$ | 5) |
| 88 | 4-CH$_3$OCH$_2$ | H | COCH$_3$ | 6) |
| 89 | 2,6-F$_2$ | H | COCH$_3$ | 7) |
| 90 | 4-Cl | H | CH$_2$Si(CH$_3$)$_3$ | 8) |
| 91 | 4-CH$_3$S | H | COCH$_3$ | 9) |
| 92 | 4-CF$_3$O | H | COCH$_3$ | 10) |

1) Values obtained by NMR spectroscopy of Compound No. 55
¹HNMR (90 MHz, DMSO-d$_6$):
1.40 (6H/2, s)   1.45 (6H/2, d)
4.60 (1H, m)    6.60 (1H/2, s)
6.80 (1H/2, s)   7.00–7.86 (7H, m)

2) Values obtained by NMR spectroscopy of Compound No. 56
¹HNMR (90 MHz, CDCl$_3$):
0.90 (3H, t)    1.00–1.50 (2H, m)
1.50–2.00 (2H, m)  4.00–4.20 (2H, m)
6.45 (1H/2, s)   6.60 (1H/2, s)
7.00–8.00 (7H, m)

3) Values obtained by NMR spectroscopy of Compound No. 83
¹HNMR (90 MHz, DMSO-d$_6$, CDCl$_3$):
0.96 (3H, t)    1.40–1.87 (2H, m)
2.56 (2H, t)    2.69 (3H/2, s)
2.76 (3H/2, s)   6.55 (1H/2, s)
6.86 (1H/2, s)   6.97–7.80 (7H, m)

4) Values obtained by NMR spectroscopy of Compound No. 85
¹HNMR (90 MHz, DMSO-d$_6$, CDCl$_3$):
2.70 (3H/2, s)   2.80 (3H/2, s)
6.53 (1H/2, s)   6.75 (1H/2, s)
6.90–7.90 (7H, m)

5) Values obtained by NMR spectroscopy of Compound No. 87
¹HNMR (90 MHz, DMSO-d$_6$, CDCl$_3$):

TABLE 1-continued

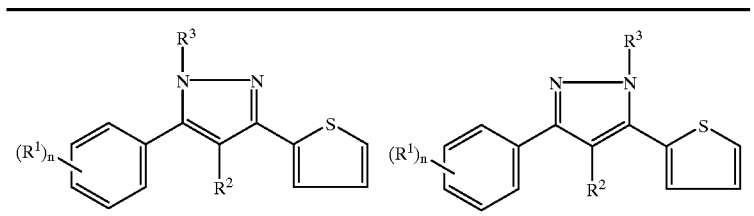

| Compound No. | (R¹)n | R² | R³ | Melting point (m.p.) ° C., $n_D^{20}$ |
|---|---|---|---|---|

2.73 (3H/2, s)  2.80 (3H/2, s)
3.87 (3H, s)  6.75 (1H/2, s)
6.77 (1H/2, s)  6.80–7.83 (7H, m)
*6) Values obtained by NMR spectroscopy of Compound No. 88
¹HNMR (90 MHz, DMSO-$d_6$, CDCl$_3$):
2.73 (3H/2, s)  2.77 (3H/2, s)
3.36 (3H, s)  4.50 (1H/2, s)
6.57 (1H/2, s)  6.83 (1H/2, s)
6.90–7.87 (7H, m)
7) Values obtained by NMR spectroscopy of Compound No. 89
¹HNMR (90 MHz, DMSO-$d_6$, CDCl$_3$):
2.77 (3H/2, s)  2.80 (3H/2, s)
6.75–7.50 (7H, m)
8) Values obtained by NMR spectroscopy of Compound No. 90
¹HNMR (90 MHz; DMSO-$d_6$, CDCl$_3$):
0.10 (9H/2, s)  0.17 (9H/2, s)
3.67 (2H/2, s)  3.80 (2H/2, s)
6.47 (1H/2, s)  6.63 (1H/2, s)
7.03–7.77 (7H, m)
9) Values obtained by NMR spectroscopy of Compound No. 91
¹HNMR (90 MHz, DMSO-$d_6$, CDCl$_3$):
2.53 (3H, s)  2.77 (3H/2, s)
2.80 (3H/2, s)  6.60 (1H/2, s)
6.83 (1H/2, s)  7.00–7.85 (7H, m)
10) Values obtained by NMR spectroscopy of Compound No. 92
¹HNMR (90 MHz, DMSO-$d_6$, CDCl$_3$):
2.70 (3H/2, s)  2.77 (3H/2, s)
6.56 (1H/2, s)  6.77 (1H/2, s)
6.90–7.87 (7H, m)

Synthesis Example 8 (intermediate)

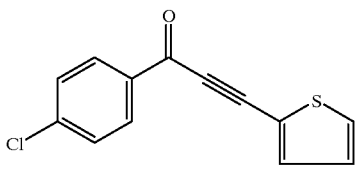

Finely-ground Molecular Sieve 4A powder (8.3 g) and pyridinium dichromate (8.3 g, 22 mM) were added to a solution of 1-(4-chlorophenyl)-3-(2-thienyl)-2-propyn-1-ol (3.8 g, 15 mM) in dry dichloromethane (30 ml), and this mixture was stirred at room temperature for 3 hours. After the completion of the reaction was confirmed, the reaction mixture was filtered through Celite, and the solvent was distilled off under reduced pressure. The resulting residue was purified by column chromatography (SiO$_2$; hexane/ethyl acetate=1/0 to 10/1) to obtain 1.3 g (5.3 mM) 1 of 1-(4-chlorophenyl)-3-(2-thienyl)-2-propyn-1-one in a 36% yield.

¹H-NMR (90 MHz, CDCl$_3$):

7.06–7.70 (5H, m);

8.17 (2H, d).

The following Table 2 shows compounds of formula (II) which can be prepared in the same manner as described in the foregoing Synthesis Example 8, together with the compound obtained in the foregoing Synthesis Example 8.

TABLE 2

(II)

| Compound No. | (R¹)n | Properties |
|---|---|---|
| II-1 | 2-F | |
| II-2 | 2-Cl | |
| II-3 | 3-Cl | |
| II-4 | 3-CH$_3$ | |
| II-5 | 4-F | |
| II-6 | 4-Cl | ¹H-NMR: (90 MHz, CDCl$_3$) 7.06–7.70 (5H, m), 8.17 (2H,d) |
| II-7 | 4-Br | |
| II-8 | 4-I | |
| II-9 | 4-CH$_3$ | |
| II-10 | 4-C$_2$H$_5$ | |
| II-11 | 4-C$_3$H$_7$-n | |
| II-12 | 4-C$_3$H$_7$-i | |
| II-13 | 4-CF$_3$ | |
| II-14 | 4-C$_2$H$_5$O | |
| II-15 | 4-C$_3$H$_7$-n-O | |
| II-16 | 4-CF$_3$O | |
| II-17 | 4-C$_6$H$_5$ | |
| II-18 | 2,4-Cl$_2$ | |

TABLE 2-continued (II)

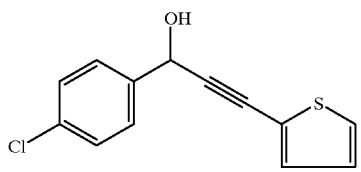

| Compound No. | (R¹)n | Properties |
|---|---|---|
| II-19 | 3,4-Cl$_2$ | |
| II-20 | 3,5-Cl$_2$ | |

Synthesis Example 9 (intermediate)

A solution of 1-(4-chlorophenyl)-1-propyn-1-ol (2.0 g, 12 mM) and 2-iodothiophene (3.8 g, 18 mM) in benzene (30 ml) was thoroughly purged by bubbling argon thereinto for 10 minutes. Thereafter, benzyltriethylammonium chloride (273 mg, 1.2 mM), tetrakistriphenylphosphine palladium (1.4 g, 1.8 mM) and a 2.5N aqueous solution of sodium hydroxide (46 ml) were added thereto, and this mixture was stirred at room temperature for 6 hours. After the addition of a saturated aqueous solution of anmmonium chloride (46 ml), the resulting mixture was stirred for 10 minutes and then extracted with dichloromethane (50 ml). The organic layer was washed with a saturated aqueous solution of sodium chloride and dried over anhydrous magnesium sulfate. Thereafter, the solvent was distilled off under reduced pressure, and the resulting residue was purified by column chromatography (SiO$_2$; hexane/ethyl acetate=1/0 to 5/1) to obtain 2.6 g (10 mM) of 1-(4-chlorophenyl)-3-(2-thienyl)-propyn-1-ol in an 84% yield.

$^1$H-NMR (90 MHz, CDCl$_3$):

2.41 (1H, d);

5.65 (1H, d);

6.82–7.56 (7H, m).

The following Table 3 shows compounds of formula (X) which can be prepared in the same manner as described in the foregoing Synthesis Example 9, together with the compound obtained in the foregoing Synthesis Example 9.

TABLE 3

(X)

| Compound No. | (R¹)n | Properties |
|---|---|---|
| X-1 | 2-F | |
| X-2 | 2-Cl | |
| X-3 | 3-Cl | |
| X-4 | 3-CH$_3$ | |
| X-5 | 4-F | |
| X-6 | 4-Cl | $^1$H-NMR (90 MHz, CDCl$_3$) 2.41 (1H, d), 5.65 (1H, d), 6.82–7.56 (7H, m) |
| X-7 | 4-Br | |
| X-8 | 4-I | |
| X-9 | 4-CH$_3$ | |
| X-10 | 4-C$_2$H$_5$ | |
| X-11 | 4C$_3$H$_7$-n | |
| X-12 | 4-C$_3$H$_7$-i | |
| X-13 | 4-CF$_3$ | |
| X-14 | 4-C$_2$H$_5$O | |
| X-15 | 4-C$_3$H$_7$-n-O | |
| X-16 | 4-CF$_3$O | |
| X-17 | 4-C$_6$H$_5$ | |
| X-18 | 2,4-Cl$_2$ | |
| X-19 | 3,4-Cl$_2$ | |
| X-20 | 3,5-Cl$_2$ | |

Synthesis Example 10 (intermediate)

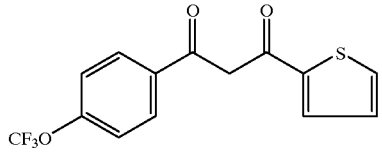

4-Trifluoromethoxyacetophenone (4.1 g, 20 mM) and ethyl 2-thiophenecarboxylate (3.1 g, 20 mM) were placed in a 300 ml eggplant type flask, and 100 ml of dehydrated tetrahydrofuran was added thereto. After this mixture was stirred at room temperature, a 60% oil suspension of sodium hydride (1.1 g, 26 mM) was slowly added thereto. Thereafter, the resulting mixture was heated under reflux for 6 hours and allowed to cool to room temperature. After 100 ml of water was added to the reaction mixture under cooling with ice, the reaction mixture was adjusted to pH 1.0 with a concentrated aqueous solution of hydrochloric acid and then extracted with 100 ml of ethyl acetate. The organic layer was washed with a saturated aqueous solution of sodium chloride and dried over anhydrous sodium sulfate. Thereafter, the solvent was distilled off under reduced pressure to obtain 6.2 g of 1-(2-thienyl)-3-(4-trifluoromethoxyphenyl)-1,3-propanedione in an almost quantitative yield.

$^1$H-NMR (90 MHz, CDCl$_3$):

6.50(1H, s);

6.90–8.03 (8H, m).

The following Table 4 shows compounds of formula (IV) which can be prepared in the same manner as described in the foregoing Synthes is Example 10, together with the compound obtained in the foregoing Synthesis Example 10.

TABLE 4

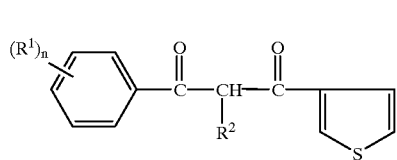

(IV)

| Compound No. | (R¹)n | R² | Properties |
|---|---|---|---|
| IV-1 | 2-F | H | ¹H-NMR (90 MHz, CDCl₃) 6.80(1H, s), 7.00–8.00(7H, m), 16.0(1H, bs) |
| IV-2 | 2-Cl | H | |
| IV-3 | 2-CF₃ | H | ¹H-NMR (90 MHz, CDCl₃) 6.40(1H, s), 7.20(1H, m), 7.50–8.00(6H, m) |
| IV-4 | 3-Cl | H | ¹H-NMR (90 MHz, CDCl₃) 6.57(1H, s), 7.10(1H, m), 7.17–7.83(6H, m), 16.0(1H, bs) |
| IV-5 | 3-CH₃ | H | ¹H-NMR (90 MHz, CDCl₃) 2.30(3H, s), 6.60(1H, s), 7.10(1H, m), 7.25–7.80(6H, m), 16.0(1H, bs) |
| IV-6 | 4-F | H | |
| IV-7 | 4-Br | H | |
| IV-8 | 4-I | H | ¹H-NMR (90 MHz, CDCl₃) 6.60(1H, s), 7.15(1H, m), 7.50–7.90(6H, m), 16.0(1H, bs) |
| IV-9 | 4-CH₃ | H | |
| IV-10 | 4-C₂H₅ | H | |
| IV-11 | 4-C₃H₇-n | H | ¹H-NMR (90 MHz, CDCl₃) 0.9(3H, t), 1.60(2H, m), 2.60(2H, t), 6.57(1H, s), 7.00–8.00(7H, m) |
| IV-12 | 4-C₃H₇-i | H | |
| IV-13 | 4-C₄H₉-n | H | ¹H-NMR (90 MHz, CDCl₃) 0.90–2.00(7H, m), 2.60(2H, t), 6.60(1H, s), 7.00–8.00(7H, m) |
| IV-14 | 4-C₄H₉-t | H | ¹H-NMR (90 MHz, CDCl₃) 1.39(9H, s), 6.60(1H, s), 7.10–8.00(7H, m) |
| IV-15 | 4-CF₃ | H | |
| IV-16 | 4-C₂H₅O | H | ¹H-NMR (90 MHz, CDCl₃) 1.26(3H, t), 4.10(2H, q), 6.63(1H, s), 6.95(2H, d), 7.15(1H, dd), 7.60(1H, d), 7.77(1H, d), 7.90(2H, d), 16.0(1H, bs) |
| IV-17 | 4-C₃H₇-n-O | H | ¹H-NMR (90 MHz, CDCl₃) 1.20(3H, t), 1.80(2H, m), 3.95(2H, t), 6.50(1H, s), 6.80(2H, d), 7.10(1H, dd), 7.50(1H, d), 7.66(1H, d), 7.80(2H, d), 16.0(1H, bs) |
| IV-18 | 4-CH₃S | H | ¹H-NMR (90 MHz, CDCl₃) 2.50(3H, s), 6.60(1H, s), 7.10(1H, m), 7.25(2H, d), 7.60(1H, d), 7.73(1H, d), 7.80(2H, d) |
| IV-19 | 4-CH₃OCH₂ | H | ¹H-NMR (90 MHz, CDCl₃) 3.43(3H, s), 4.50(2H, s), 6.66(1H, s), 7.20(1H, dd), 7.46(2H, d), 7.66(1H, d), 7.83(1H, d), 7.93(2H, d), 16.0(1H, bs) |
| IV-20 | 4-C₂H₅OCH₂ | H | ¹H-NMR (90 MHz, CDCl₃) 1.20(3H, t), 3.50(2H, q), 4.50(2H, s), 6.63(1H, s), 7.10(1H, dd), 7.40(2H, d), 7.56(1H, d), 7.73(1H, d), 7.90(2H, d) |
| IV-21 | 4-CH₃SCH₂ | H | |
| IV-22 | 4-CHF₂O | H | |
| IV-23 | 4-CF₃O | H | ¹H-NMR (90 MHz, CDCl₃) 6.50(1H, s), 6.90–8.03(8H, m) |
| IV-24 | 4-CF₃CH₂O | H | |
| IV-25 | 4-CH₃OCH₂O | H | |
| IV-26 | 4-C₆H₅ | H | |
| IV-27 | 4(4-F—C₆H₄) | H | |
| IV-28 | 4-(4-CH₃—C₆H₄) | H | |
| IV-29 | 2,4-Cl₂ | H | |
| IV-30 | 3,4-Cl₂ | H | |
| IV-31 | 3,5-Cl₂ | H | |
| IV-32 | 2,6-F₂ | H | |
| IV-33 | 2,4-F₂ | H | ¹H-NMR (90 MHz, CDCl₃) 6.50–8.30(7H, m) |
| IV-34 | 3,4-F₂ | H | |
| IV-35 | 2,4,6-F₃ | H | |
| IV-36 | 2,4,6-Cl₃ | | |
| IV-37 | 4-CF₃, 2,6-F₂ | H | |

Synthesis Example 11 (intermediate)

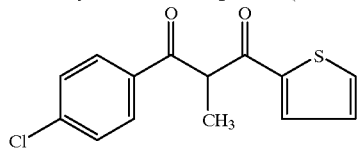

A 1 molar tetrahydrofuran solution of tetrabutylammonium fluoride (Bu4NF) (3.8 ml, 3.8 mM) was added to a solution of 1-(4-chlorophenyl)-3-(2-thienyl)-1,3-propanedione (1 g, 3.8 mM) in dehydrated tetrahydrofuran (30 ml) at room temperature, and this mixture was stirred at room temperature for 1 hour. The solvent was distilled off under reduced pressure, and a homogeneous solution was formed by adding 30 ml of chloroform to the reside. Then, methyl iodide (MeI) (1.1 g, 7.6 mM) was added thereto, and this mixture was stirred at room temperature for 3 hours. Thereafter, the solvent was distilled off under reduced pressure, and the resulting residue was purified by column chromatography (SiO₂; hexane-ethyl acetate solution) to obtain 760 mg (2.7 mM) of the desired compound, 1-(4-chlorophenyl)-2-methyl-3-(2-thienyl)-1,3-propanedione, in a 71% yield.

¹H-NMR (90 MHz, CDCl₃):

1.41 (3H, d);

5.60 (1H, q);

7.31 (1H, t);

7.60 (2H, d);

7.87–8.06 (4H, m).

Synthesis Example 12 (intermediate)

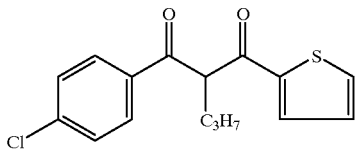

Propyl iodide (1.8 g, 11 mM) was added to a solution of 1-(4-chlorophenyl)-3-(2-thienyl)-1,3-propanedione (2.0 g, 7.6 mnM) in a dehydrated tetrahydrofuran (30 ml)-dimethylformamide (20 ml) mixture. Then, a 60% oil suspension of sodium hydride (360 mg, 9.0 mM) was slowly added thereto. This mixture was stirred at room temperature for 10 minutes, heated under reflux for 3 hours, and allowed to cool. After 60 ml of water was added thereto, the resulting mixture was adjusted to pH 1.0 with concentrated hydrochloric acid and then extracted with 100 ml of ethyl acetate. The organic layer was washed with a saturated aqueous solution of sodium chloride and dried over anhydrous sodium sulfate. Thereafter, the solvent was distilled off under reduced pressure, and the resulting residue was purified by column chromatography (SiO₂; hexane-ethyl acetate solvent mixture) to obtain 1.4 g (4.6 mM) of the desired compound, 1-(4-chlorophenyl)-2-propyl-3-(2-thienyl)-1,3-propanedione, in a 60% yield.

¹H-NMR (90 MHz, CDCl₃):

0.96 (3H, t);

1.23–1.60 (2H, m);

1.97–2.33 (2H, m);

4.93 (1H, t);

7.03–7.93 (7H, m).

The following Table 5 shows compounds of formula (IV-a) which can be prepared in the same manner as described in the foregoing Synthesis Examples 11 and 12, together with the compounds obtained in the foregoing Synthesis Examples 11 and 12.

TABLE 5

(IV-a)

| Compound No. | $(R^1)_n$ | $R^2$ | Properties |
|---|---|---|---|
| IV-a-1 | 4-F | CH₃ | |
| IV-a-2 | 4-Cl | CH₃ | ¹H-NMR (90 MHz, CDCl₃) 1.41(3H, d), 5.60(1H, q), 7.31(1H, t), 7.60(2H, d), 7.87–8.06(4H, m) |
| IV-a-3 | 4-Cl | C₂H₅ | |
| IV-a-4 | 4-Cl | C₃H₇-n | ¹H-NMR (90 MHz, CDCl₃) 0.96(3H, t), 1.23–1.60(2H, m), 1.97–2.33(2H, m), 4.93(1H, t), 7.03–7.93(7H, m) |
| IV-a-5 | 4-Cl | CH₃SCH₂ | ¹H-NMR (90 MHz, CDCl₃) 2.10(3H, s), 3.30(2H, dd), 5.20(1H, m), 7.10(1H, dd), 7.40(2H, d), 7.60(1H, d), 7.70(1H, d), 7.90(2H, d) |
| IV-a-6 | 4-Cl | CH₃OCH₂ | |

Synthesis Example 13

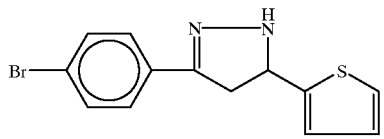

1-(4-Bromophenyl)-3-(2-thienyl)-2-propen-1-one (3.0 g, 10.2 mmol) and hydrazine hydrate (1.0 g, 20 mmol) were added to ethanol (30 ml) and heated under reflux for 3 hours. After the mixture was allowed to cool to room temperature, the solvent was distilled off to obtain 3.0 g (98%) of the desired 3-(4-bromophenyl)-5-(2-thienyl)-pyrazoline in the form of a resinous material.

¹H-NMR (90 MHz, CDCl₃):

3.07 (1H, dd);

3.47 (1H, dd);

5.20 (1H, dd);

6.10 (1H, m);

6.97 (2H, m);

7.15 (1H, m);

7.48 (4H, bs).

The following Table 6 shows compounds of formula (VII-a) which can be prepared in the same manner as described in the foregoing Synthesis Example 13, together with the compound obtained in the foregoing Synthesis Example 13.

TABLE 6

(VII-a)

[Structure: pyrazoline with (R¹)n-phenyl, R², R³, and thienyl groups]

| Compound No. | (R¹)n | R² | R³ | Properties |
|---|---|---|---|---|
| VIIa-1 | 2-F | H | H | |
| VIIa-2 | 2-Cl | H | H | |
| VIIa-3 | 2-CF$_3$ | H | H | |
| VIIa-4 | 3-Cl | H | H | |
| VIIa-5 | 3-CH$_3$ | H | H | |
| VIIa-6 | 4-F | H | H | |
| VIIa-7 | 4-Br | H | H | $^1$H-NMR (90 MHz, CDCl$_3$) 3.07(1H, dd), 3.47(1H, dd), 5.20(1H, dd), 6.10(1H, m), 6.97(2H, m), 7.15(1H, m), 7.48(4H, bs) |
| VIIa-8 | 4-I | H | H | |
| VIIa-9 | 4-CH$_3$ | H | H | |
| VIIa-10 | 4-C$_2$H$_5$ | H | H | |
| VIIa-11 | 4-C$_3$H$_7$-n | H | H | |
| VIIa-12 | 4-C$_3$H$_7$-i | H | H | |
| VIIa-13 | 4-C$_4$H$_9$-n | H | H | |
| VIIa-14 | 4-C$_4$H$_9$-t | H | H | |
| VIIa-15 | 4-CF$_3$ | H | H | |
| VIIa-16 | 4-C$_2$H$_5$O | H | H | |
| VIIa-17 | 4-C$_3$H$_7$-n-O | H | H | |
| VIIa-18 | 4-CH$_3$S | H | H | |
| VIIa-19 | 4-CH$_3$OCH$_2$ | H | H | |
| VIIa-20 | 4-C$_2$H$_5$OCH$_2$ | H | H | |
| VIIa-21 | 4-CH$_3$SCH$_2$ | H | H | |
| VIIa-22 | 4-CHF$_2$O | H | H | |
| VIIa-23 | 4-CF$_3$O | H | H | |
| VIIa-24 | 4-CF$_3$CH$_2$O | H | H | |
| VIIa-25 | 4-C$_6$H$_5$ | H | H | |
| VIIa-26 | 4-(4-F—C$_6$H$_4$) | H | H | |
| VIIa-27 | 2,4-Cl$_2$ | H | H | |
| VIIa-28 | 3,4-Cl$_2$ | H | H | |
| VIIa-29 | 3,5-Cl$_2$ | H | H | |
| VIIa-30 | 2,6-F$_2$ | H | H | |
| VIIa-31 | 2,4-F$_2$ | H | H | |
| VIIa-32 | 3,4-F$_2$ | H | H | |
| VIIa-33 | 2,4,6-F$_3$ | H | H | |
| VIIa-34 | 2,4,6-Cl$_3$ | H | H | |
| VIIa-35 | 4-CF$_3$, 2,6-F$_2$ | H | H | |
| VIIa-36 | 4-Cl | CH$_3$ | H | |
| VIIa-37 | 4-Cl | C$_2$H$_5$ | H | |
| VIIa-38 | 4-Cl | C$_3$H$_7$-n | H | |
| VIIa-39 | | | | |

Synthesis Example 14

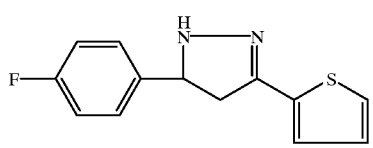

3-(4-Fluorophenyl)-1-(2-thienyl)-2-propen-1-one (3.5 g, 15 mM) and hydrazine hydrate (1.5 g, 30 mM) were added to ethanol (30 ml) and heated under reflux for 3 hours. After the mixture was allowed to cool to room temperature, the solvent was distilled off to obtain 3.6 g (98%) of the desired 5-(4-fluorophenyl)-3-(2-thienyl)-pyrazoline in the form of a pale-yellow oil, $n_D^{20}$=1.6364.

The following Table 7 shows compounds of formula (VII-b) which can be prepared in the same manner as described in the foregoing Synthesis Example 14, together with the compound obtained in the foregoing Synthesis Example 14.

TABLE 7

(VII-b)

[Structure: pyrazoline with (R¹)n-phenyl, R², R³, and thienyl groups]

| Compound No. | (R¹)n | R² | R³ | Properties |
|---|---|---|---|---|
| VIIb-1 | 2-F | H | H | |
| VIIb-2 | 2-Cl | H | H | |
| VIIb-3 | 2-CF$_3$ | H | H | |
| VIIb-4 | 3-Cl | H | H | |
| VIIb-5 | 3-CH$_3$ | H | H | |
| VIIb-6 | 4-F | H | H | $n_D^{20}$ 1.6364 |
| VIIb-7 | 4-Br | H | H | |
| VIIb-8 | 4-I | H | H | |
| VIIb-9 | 4-CH$_3$ | H | H | |
| VIIb-10 | 4-C$_2$H$_5$ | H | H | |
| VIIb-11 | 4-C$_3$H$_7$-n | H | H | |
| VIIb-12 | 4-C$_3$H$_7$-i | H | H | |
| VIIb-13 | 4-C$_4$H$_9$-n | H | H | |
| VIIb-14 | 4-C$_4$H$_9$-t | H | H | |
| VIIb-15 | 4-CF$_3$ | H | H | |
| VIIb-16 | 4-C$_2$H$_5$O | H | H | |
| VIIb-17 | 4-C$_3$H$_7$-n-O | H | H | |
| VIIb-18 | 4-CH$_3$S | H | H | |
| VIIb-19 | 4-CH$_3$OCH$_2$ | H | H | |
| VIIb-20 | 4-C$_2$H$_5$OCH$_2$ | H | H | |
| VIIb-21 | 4-CH$_3$SCH$_2$ | H | H | |
| VIIb-22 | 4-CHF$_2$O | H | H | |
| VIIb-23 | 4-CF$_3$O | H | H | |
| VIIb-24 | 4-CF$_3$CH$_2$O | H | H | |
| VIIb-25 | 4-C$_6$H$_5$ | H | H | |
| VIIb-26 | 4-(4-F—C$_6$H$_4$) | H | H | |
| VIIb-27 | 2,4-Cl$_2$ | H | H | |
| VIIb-28 | 3,4-Cl$_2$ | H | H | |
| VIIb-29 | 3,5-Cl$_2$ | H | H | |
| VIIb-30 | 2,6-F$_2$ | H | H | |
| VIIb-31 | 2,4-F$_2$ | H | H | |
| VIIb-32 | 3,4-F$_2$ | H | H | |
| VIIb-33 | 2,4,6-F$_3$ | H | H | |
| VIIb-34 | 2,4,6-Cl$_3$ | H | H | |
| VIIb-35 | 4-CF$_3$, 2,6-F$_2$ | H | H | |
| VIIb-36 | 4-Cl | CH$_3$ | H | |
| VIIb-37 | 4-Cl | C$_2$H$_5$ | H | |
| VIIb-38 | 4-Cl | C$_3$H$_7$-n | H | |
| VIIb-39 | | | | |

Test Example 1

Test on Root-knot Nematodes (test by soaking nematodes in test solutions)

Preparation of test solutions:

Test solutions were prepared by dissolving 10 mg each of active compounds in 0.05 ml of a mixture of a solvent (dimethylformamide) and emulsifiers (Sorpol SD and Sorpol BDB), and adding 10 ml of water thereto.

Testing procedure:

1 ml each of the test solutions were placed in test tubes, and 9 ml of an aqueous solution containing about 500 southern root-knot nematodes to each test tube (so as to give a final concentration of 100 ppm). Then, these test tubes were allowed to stand in a thermostatic chamber at 25 and observed under the microscope after 2 days.

According the degree of immovableness (or stiffness) of the nematodes, the controlling effect was evaluated on the following basis.

A: 100–70% of the nematodes were immovable.
B: 70–40% of the nematodes were immovable.
C: Less than 40% of the nematodes were immovable.
D: 0% of the nematodes were immovable.

The results thus obtained are shown below.

Results:

Compound Nos. 6, 7, 9, 10, 11, 16, 19, 25, 26, 37, 45, 49, 58, 61, 63, 64, 65, 66, 67, 68, 69, 70, 71, 72, 74, 75, 77, 80, 82, 83, 84, 85, 87, 88, and 89, exhibited the rating A at an active ingredient concentration of 100 ppm.

Test Example 2

Test on Root-knot Nematodes (soil pot test)

Preparation of test solutions:

Fine granular formulations were prepared by impregnating 99 parts of pumice with 1 part each of active compounds.

Testing procedure:

Each of the active compounds prepared in the above-described manner was added to soil infested with southern root-knot nematodes so as to give an active ingredient concentration of 50 ppm, and intimately blended therein. This soil was charged into pots having an area of 1/5000 are, and about 20 tomato seeds (of the Kurihara variety) were sown in each pot. Tomato plants were grown in a greenhouse and, after 4 weeks, extracted so as not to injure their roots. Then, the root knot index and the controlling effect for each active compound were determined in the following manner.

Degree of damage

0: No knot was formed (perfectly controlled).
1: Knots were formed to a slight degree.
2: Knots were formed to a moderate degree.
3: Knots were formed to a heavy degree.
4: Knots were formed to the heaviest degree (corresponding to no treatment).

$$\text{Root knot index} = \frac{\sum [(\text{degree of damage}) \times (\text{number of plants})]}{(\text{Total number of plants tested}) \times 4} \times 100$$

$$\text{Controlling effect} = \frac{(\text{root knot index of untreated plot}) - (\text{root knot index of treated plot})}{\text{root knot index of untreated plot}} \times 100$$

According to the value of the controlling effect, the effectiveness was rated on the following basis.

a: The controlling effect was in the range of 100 to 71%.
b: The controlling effect was in the range of 70 to 50%.
c: The controlling effect was less thai 50%.
d: The controlling effect was 0%.

The results thus obtained are shown in Table 8.

TABLE 8

| Compound No. | Active ingredient concentration (ppm) | Evaluation |
| --- | --- | --- |
| 6 | 50 | a |
| 7 | 50 | a |
| 9 | 50 | a |
| 11 | 50 | a |
| 26 | 50 | a |
| 58 | 50 | a |
| 68 | 50 | a |
| 75 | 50 | a |
| Comparative Compound-1 | 50 | c |

TABLE 8-continued

| Compound No. | Active ingredient concentration (ppm) | Evaluation |
| --- | --- | --- |
| Comparative Compound-2 | 50 | d |

Comparative compound 1: 3-(2-Thienyl)-5-phenyl-1H-pyrazole.
Comparative compound 2: 3-(2-Thienyl)-5-(4-methoxyphenyl)-1H-pyrazole.

Test Example 3

Test on *Trichinella spiralis*, Owen, Larvae

Testing procedure

The method was carried out, in accordance with a method described in Tropenmed. Parasitol., vol. 32 (1981), 31–34, Jenkins, D. C., and Carrington, T. S. *T. spiralis* larvae were isolated from skeletal muscles and diaphragms of SPF/CFW1 mice and stored in sodium chloride solution (90 g/l) supplemented with Canested (20 μg/ml). The larvae (20 per estimation) were incubated in 2 ml of a solution with the following composition: Casitone 20; yeast extract 10; glucose 5; potassium dihydrogen phosphate 0.8; dipotassium hydrogen phosphate 0.8 g/l in water (500 ml; pH 7.2) and supplemented with Sisomycin (10 mg/l) and Canesten (1 mg/l).

The test compound (10 mg) was dissolved in dimethylsulfoxide (0.5 ml) and added to the incubation medium containing the larvae to give final concentrations of 100 μg/ml. The mixture was incubated at 19° C. for five days, after which activity was assessed according to Jenkins and Carrington a scale 1–3 where 1=weak activity (fewer live larvae than in the untreatted control); 2=good acitivity (>=50% more dead larvae than in the untreated control) and 3=full acivity (all larvae dead).

The results thus obtained are shown in Table 9

TABLE 9

| Compound No. | Active ingredient μg/ml | Evolution |
| --- | --- | --- |
| 6 | 100 | 2 |
| 46 | 100 | 2 |
| 49 | 100 | 2 |

Test Example 4

Test on *Nippostrongylus brasiliensis*, Lane, Adult

Testing procedure

The meethod was carried out, in accordance with a method described in Parasitol. Res., vol. 73 (1987) 191, Rapson, E. B. et al.

*N. brasiliensis* adult worms are isolated from the small intestine of female Wister rats and stored in sodium chloride solution (90 g/l) supplemented with Canesten (2 mg/l) and Sisomycin (20 mg/l). Worms (five male and five female) were incubated, according to the method of Rapson et al, and the incubation medium was ajusted so as to give final concentrations of 100 μg/ml. The resulting incubation medium was assessed for acetylcholine esterase activity, as performed by Rapso et al. using a scale 0–3 where 0=no activity (<50% enzyme inhibition) and 1, 2 and 3 weak, good and full activity (50–75, >75 and 100% enzyme inhibition, respectively).

The results thus obtained are shown in Table 10.

TABLE 10

| Compound No. | Active ingredient µg/ml | Evalution |
|---|---|---|
| 6 | 100 | 3 |
| 9 | 100 | 3 |
| 46 | 100 | 3 |
| 49 | 100 | 3 |

Test Example 5

Meloidogyne Test

Test nematode: Meloidogyne incognita
Solvent: 4 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier is added and the concentrate is diluted with water to the desired concentration.

The active compound preparation is intimately mixed with soil which is heavily infected with the test nematodes. The treated soil is transferred into pots, lettuce seeds are sown and the pots are kept in the greenhouse.

After the desired time the lettuce roots are checked for infestation with nematodes (root galls) and the efficacy of the active compound in % is determined. The efficacy is 100% when infestation is avoided completely and 0% when infestation level is just as high as in the control plants in untreated but equally infested soil. The results are shown in table 11.

TABLE 11

| Compound | Active compound concentration (ppm) | kill (%) |
|---|---|---|
| (structure shown) | 5 | 100 |

Test Example 6

Meloidogyne test

Test nematode: Meloidogyne incognita
Solvent: 31 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier is added and the concentrate is diluted with water to the desired concentration.

The active compound preparation is intimately mixed with soil which is heavily infected with the test nematodes. The treated soil is transferred into pots, lettuce seeds are sown and the pots are kept in the greenhouse.

After the desired time the lettuce roots are checked for infestation with nematodes (root galls) and the efficacy of the active compound in % is determined. The efficacy is 100% when infestation is avoided completely and 0% when infestation level is just as high as in the control plants in untreated but equally infested soil.

The results are shown in table 12.

TABLE 12

| Compound | active compound concentration (ppm) | kill in % after 14 d |
|---|---|---|
| (structure shown) | 20 | 100 |

Formulation Example 1 (granules)

25 parts of water is added to a mixture composed of 10 parts of Compound No. 7 according to the present invention, 30 parts of bentonite (montmorillonite), 58 parts of talc, and 2 parts of lignin sulfonate. This mixture is kneaded well, granulated to a size of 10–40 mesh by means of an extrusion granulator, and dried at 40–50° C. to obtain granules.

Formulation Example 2 (granules)

95 parts of a particulate clay mineral having a particle size distribution of 0.2 to 2 mm is placed in a rotary mixer and tumbled. This clay mineral is uniformly wetted by spraying thereon 7.5 parts of Compound No. 7 according to the present invention together with a liquid diluent, and then dried at 40–50. to obtain granules.

Formulation Example 3 (emulsion)

30 parts of Compound No. 11 according to the present invention, 50 parts of xylene, 8 parts of polyoxyethylene alkylphenyl ether, and 7 parts of calcium alkylbenzene-sulfonate are mixed and stirred to obtain an emulsion.

Formulation Example 4 (wettable powder)

15 parts of Compound No. 6 according to the present invention, 80 parts of a 1:5 mixture of white carbon (finely powdered hydrous amorphous silicon oxide) and powdered clay, 2 parts of sodium alkylbenzenesulfonate, and 3 parts of sodium alkylnaphthalenesulfonate-formalin condensate are milled and blended to obtain a wettable powder.

What is claimed is:

1. A compound of the formula (I)

(I)

(structure shown)

wherein $R^1$ represents halogen, $C_{1-6}$ alkyl, $C_{1-5}$ haloalkyl, $C_{2-6}$ alkoxy, $C_{1-4}$ alkylthio, $C_{2-5}$ alkenyloxy, $C_{3-5}$ alkenyloxy, $C_{2-6}$ (total carbon number) alkoxyalkyl, $C_{2-6}$ (total carbon number) alkylthioalkyl, $C_{1-5}$ haloalkoxy, $C_{2-6}$ (total carbon number) alkoxyalkoxy, hydroxy or optionally substituted phenyl, $R^2$ represents hydrogen, halogen, $C_{1-5}$ alkyl, $C_{2-6}$ (total carbon number) alkoxyalkyl, $C_{2-6}$ (total carbon number) alkylthioalkyl, $C_{2-6}$ (total carbon number) alkylsulfinylalkyl, $C_{2-6}$ (total carbon number) alkylsulfonylalkyl or $C_{1-5}$ haloalkyl, $R^3$ represents hydrogen, $C_{1-5}$ alkyl, —$COR^4$, $COOR^5$, $CH(OR^6)_2$ or $CH_2Si(R^7)_3$, $R^4$ represents $C_{1-10}$ alkyl, $C_{1-6}$ haloalkyl, $C_{2-6}$ alkenyl, optionally substituted $C_{3-6}$ cycloalkyl, $C_{2-6}$ (total carbon number) alkoxyalkyl, $C_{2-6}$ (total carbon number) alkylthioalkyl, optionally substituted phenyl, $C_{1-5}$ alkylamino, di-($C_{1-6}$ alkyl)amino or optionally substituted phenylamino, $R^5$ represents $C_{1-7}$ alkyl, $R^6$ and $R^7$ represent $C_{1-6}$ alkyl, and n is 1, 2 or 3, and when n is 2 or 3, the corresponding number (n) of $R^1$ radicals may be the same or different with the proviso that 2-[5-(2-thienyl)-1H-pyrzaol-3-yl]-phenol is excluded.

2. A compound of formula (I) according to claim 1, wherein $R^1$ represents fluoro, chloro, bromo, iodo, $C_{1-4}$ alkyl, $C_{1-3}$ haloalkyl, $C_{2-4}$ alkoxy, $C_{1-3}$ alkylthio, $C_{2-3}$ alkenyloxy, $C_{3-4}$ alkenyloxy, $C_{2-4}$ (total carbon number) alkoxyalkyl, $C_{2-4}$ (total carbon number) alkylthioalkyl, $C_{1-3}$ haloalkoxy, $C_{2-4}$ (total carbon number) alkoxyalkoxy, hydroxy, optionally halogen-substituted phenyl or optionally $C_{1-3}$ alkyl-substituted phenyl, $R^2$ represents hydrogen, fluoro, chloro, bromo, $C_{1-4}$ alkyl, $C_{2-4}$ (total carbon number) alkoxyalkyl, $C_{2-4}$ (total carbon number) alkylthioalkyl, $C_{2-4}$ (total carbon number) alkylsulfinylalkyl, $C_{2-4}$ (total carbon number) alkylsulfonylalkyl or $C_{1-3}$ haloalkyl, $R^3$ represents hydrogen, $C_{1-5}$ alkyl, —$COR^4$, $COOR^5$, $CH(OR^6)_2$ or $CH_2Si(R^7)_3$, $R^4$ represents $C_{1-5}$ alkyl, $C_{1-4}$ haloalkyl, $C_{2-3}$ alkenyl, cyclopropyl, fluoro-substituted cyclopropyl, $C_{2-4}$ (total carbon number) alkoxyalkyl, $C_{2-4}$ (total carbon number) alkylthioalkyl, optionally halogen-substituted phenyl, optionally $C_{1-3}$ fluoroalkyl-substituted phenyl, $C_{1-3}$ alkylamino, di-($C_{1-4}$ alkyl)amino or optionally chloro-substituted phenylamino, $R^5$ represents $C_{1-5}$ alkyl, $R^6$ and $R^7$ represent $C_{1-4}$ alkyl, and n is 1, 2 or 3, and when n is 2 or 3, $R^1$ radicals may be the same or different.

3. A compound of formula (I) according to claim 1, wherein $R^1$ represents fluoro, chloro, bromo, iodo, $C_{1-4}$ alkyl, fluoro- or substituted $C_{1-3}$ alkyl, $C_{2-3}$ alkoxy, $C_{1-2}$ alkylthio, allyloxy, propargyloxy, $C_{2-3}$ (total carbon number) alkoxyalkyl, $C_{2-3}$ (total carbon number) alkylthioalkyl, fluoro-substituted $C_{1-3}$ alkoxy, $C_{2-3}$ (total carbon number) alkoxyalkoxy, hydroxy or optionally fluoro- or methyl- substituted phenyl, $R^2$ represents hydrogen, fluoro, chloro, bromo, $C_{1-4}$ alkyl, $C_{2-3}$ (total carbon number) alkoxyalkyl, $C_{2-3}$ (total carbon number) alkylthioalkyl, $C_{2-3}$ (total carbon number) alkylsulfinylalkyl, $C_{2-3}$ (total carbon number) alkylsulfonylalkyl or fluoro-substituted $C_{1-3}$ alkyl, $R^3$ represents hydrogen, $C_{1-4}$ alkyl, —$COR^4$, —$COOR^5$, $CH(OR^6)_2$ or $CH_2Si(R^7)_3$, $R^4$ represents $C_{1-5}$ alkyl, $C_{1-4}$ haloalkyl, $C_{2-3}$ alkenyl, cyclopropyl, fluoro-substituted cyclopropyl, $C_{2-3}$ (total carbon number) alkoxyalkyl, $C_{2-3}$ (total carbon number) alkylthioalkyl, optionally fluoro-substituted phenyl, optionally trifluoromethyl-substituted phenyl, $C_{1-2}$ alkylamino, di-($C_{1-2}$ alkyl)amino or optionally parachloro-substituted phenylamino, $R^5$ represents $C_{1-4}$ alkyl, $R^6$ represents $C_{1-2}$ alkyl, $R^7$ represents methyl and n is 1, 2 or 3, and when n is 2 or 3, $R^1$ radicals may be the same or different.

4. A process for the preparation of the compounds of the formula (I)

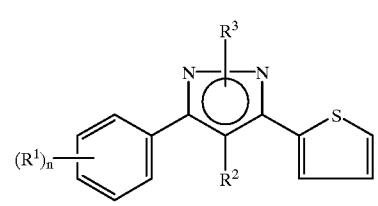

(I)

wherein $R^1$ represents halogen, $C_{1-6}$ alkyl, $C_{1-5}$ haloalkyl, $C_{2-6}$ alkoxy, $C_{1-4}$ alkylthio, $C_{2-5}$ alkenyloxy, $C_{3-5}$, $C_{2-6}$ (total carbon number) alkoxyalkyl, $C_{2-6}$ (total carbon number) alkylthioalkyl, $C_{1-5}$ haloalkoxy, $C_{2-6}$ (total carbon number) alkoxyalkoxy, hydroxy or optionally substituted phenyl, $R^2$ represents hydrogen, halogen, $C_{1-5}$ alkyl, $C_{2-6}$ (total carbon number) alkoxyalkyl, $C_{2-6}$ (total carbon number) alkylthioalkyl, $C_{2-6}$ (total carbon number) alkylsulfinylalkyl, $C_{2-6}$ (total carbon number) alkylsulfonylalkyl or $C_{1-5}$ haloalkyl, $R^3$ represents hydrogen, $C_{1-5}$ alkyl, —$COR^4$, $COOR^5$, $CH(OR^6)_2$ or $CH_2Si(R^7)_3$, $R^4$ represents $C_{1-10}$ alkyl, $C_{1-6}$ haloalkyl, $C_{2-6}$ alkenyl, optionally substituted $C_{3-6}$ cycloalkyl, $C_{2-6}$ (total carbon number) alkoxyalkyl, $C_{2-6}$ (total carbon number) alkylthioalkyl, optionally substituted phenyl, $C_{1-5}$ alkylamino, di-($C_{1-6}$ alkyl)amino or optionally substituted phenylamino, $R^5$ represents $C_{1-7}$ alkyl, $R^6$ and $R^7$ represent $C_{1-6}$ alkyl, and n is 1, 2 or 3, and when n is 2 or 3, the corresponding number (n) of $R^1$ radicals may be the same or different, wherein, a) when $R^3$ is hydrogen:
compounds of the formula

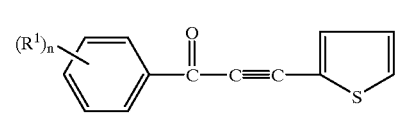

(II)

wherein $R^1$ and n are as defined above, are reacted with a compound of the formula $NH_2$—$NH_2$ (III)

in the presence of suitable diluent, or b) when R³ is hydrogen:
compounds of the formula

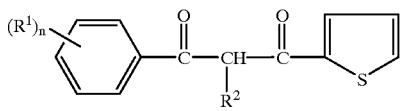
(IV)

wherein R¹, R² and n are as defined above, are reacted with the aforementioned compound of the formula (III) in the presence of suitable diluent, or c) when R³ is a radical as defined above but other than hydrogen
compounds of formula

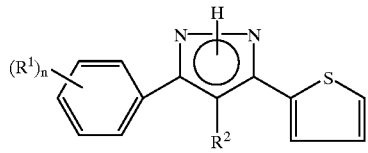
(V)

wherein R¹, R² and n are as defined above, are reacted with the compounds of the formula

R³—X (VI)

wherein R³ is a radical as defined above but other than hydrogen, and X is halogen,
in the presence of suitable diluent, and or d) compounds of the formula

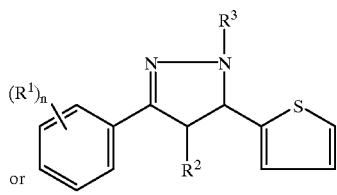
(VIIa)

or

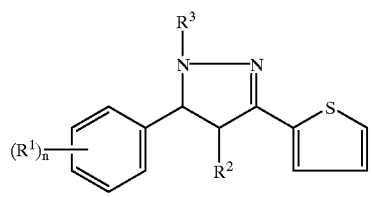
(VIIb)

wherein R¹, R², R³ and n are as defined above, are oxidized, or e) when R² is alkylsulfinylalkyl or alkylsulfonylalkyl compounds of the formula

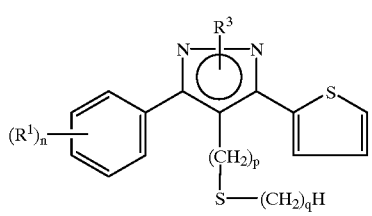
(VIII)

wherein R¹, R³ and n are as defined above, p is 1, 2 or 3, q is 1, 2, 3, 4 or 5, and $2 \leq p+q \leq 6$, are oxidized.

5. A nematicidal composition, comprising one more pyrazole compounds of the formula (I) according to claim 1.

6. A process for combating nematodes, wherein pyrazoles of the formula (I) according to claim 1 are allowed to act on nematodes and/or their habitat.

7. An anthelmintic composition comprising one or more pyrazole compounds of the formula (I) according to claim 1.

8. A process for combating parasites, wherein pyrazoles of the formula (I) according to claim 1 are allowed to act on parasites and/or their habitat.

9. A process for the preparation of anthelmintic compositions, wherein pyrazoles of the formula (I) according to claim 1 are mixed with extenders and/or surface active agents.

10. A process according to claim 4, wherein step a) occurs in the presence of an acid catalyst; step b) occurs in the presence of an acid catalyst; and step c) occurs in the presence of an acid binding agent.

11. A compound according to claim 1, wherein n is 1 then R¹ is other than an ortho-hydroxy.

12. A compound according to claim 1, wherein R¹ represents halogen, $C_{1-6}$ alkyl, $C_{1-5}$ haloalkyl, $C_{2-6}$ alkoxy, $C_{1-4}$ alkylthio, $C_{2-5}$ alkenyloxy, $C_{3-5}$, $C_{2-6}$ (total carbon number) alkoxyalkyl, $C_{2-6}$ (total carbon number) alkylthioalkyl, $C_{1-5}$ haloalkoxy, $C_{2-6}$ (total carbon number) alkoxyalkoxy or represents unsubstituted or halogen- or $C_{1-3}$ alkyl-substituted phenyl.

13. A compound according to claim 1, wherein R¹ is selected from the group consisting of 4-OH, 2-F, 4-F, 2-CF₃, 4-CF₃, 2,4-F₂, 2,6-F₂, 3,4-F₂, 2,4,6-F₃, 2-Cl 3-Cl, 4-Cl, 2,4-C₂, 3,4-Cl₂, 3,5-Cl₂, 2,4,6-Cl₃, 4-Br, 4-I, 4-CF₃-2,6-F₂, 3-CH₃, 4-CH₃, 4-C₂H₅, 4-C₃H₇-n, 4-C₃H₇—I, 4-C₄H₉-n, 4-C₄H₉-t, 4-C₆H₅, 4-(4-F—C₆H₄), 4-(4-CH₃—C₆H₄) 4-C₂H₅O, 4-C₃H₇O, 4-CH₃OCH₂O, 4-CH₂=CHCH₂O, 4-CH☐CCH₂O, 4-CH₃OCH₂, 4-C₂H₅OCH₂, 4-CH₃S, 4-CH₃SCH₂, 4-CHF₂O, 4-CF₃O, 4-CF₃CH₂O and 4-CHF₂CF₂CH₂O.

14. A compound according to claim 13, wherein R² is selected from the group consisting of H, F, Cl, Br, CH₂CF₃, CH₂CF₂CHF₂, CH₃, C₂H₅, C₃H₇-n, CH₂OCH₃, CH₂SCH₃, CH₂SOCH₃, and CH₂SO₂CH₃ and R³ is selected from the group consisting of H, CH₃, C₃H₇-i, C₄H₉-n, COCH₃, COC₂H₅, COC₃H₇-n, COC₃H₇-i, COC₄H₉-n, COC₄H₉-t, COC₅H₁₁-n, COCH=CH—CH₃, CH(OCH₃)₂,

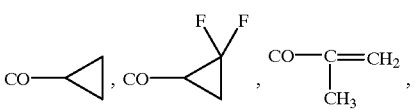

COCH₂OCH₃, COCH₂SCH₃, COC₆H₅, CO—C₆H₄-4-F, CO—C₆H₄-4-CF₃, CONHC₂H₅, CONHC₆H₄-4-Cl, COOC₄H₉-t, COCH₂Cl, CH(OC₂H₅)₂, and CH₂Si(CH₃)₃.

* * * * *